US005681811A

United States Patent [19]

Ekwuribe

[11] Patent Number: 5,681,811
[45] Date of Patent: Oct. 28, 1997

[54] CONJUGATION-STABILIZED THERAPEUTIC AGENT COMPOSITIONS, DELIVERY AND DIAGNOSTIC FORMULATIONS COMPRISING SAME, AND METHOD OF MAKING AND USING THE SAME

[75] Inventor: Nnochiri Nkem Ekwuribe, Cary, N.C.

[73] Assignee: Protein Delivery, Inc., Durham, N.C.

[21] Appl. No.: 509,422

[22] Filed: Jul. 31, 1995

Related U.S. Application Data

[60] Continuation-in-part of Ser. No. 276,890, Jul. 19, 1994, Pat. No. 5,438,040, which is a division of Ser. No. 59,701, May 10, 1993, Pat. No. 5,359,030.

[51] Int. Cl.$^6$ .................................................. A61K 37/16
[52] U.S. Cl. ........................................................... 514/8
[58] Field of Search .................................................. 514/8

[56] References Cited

U.S. PATENT DOCUMENTS

| | | | |
|---|---|---|---|
| 3,256,153 | 6/1966 | Heimlich | 167/82 |
| 4,003,792 | 1/1977 | Mills et al. | 195/63 |
| 4,044,196 | 8/1977 | Hüper et al. | 526/271 |
| 4,179,337 | 12/1979 | Davis et al. | 435/181 |
| 4,410,547 | 10/1983 | Ueno et al. | 424/317 |
| 4,585,754 | 4/1986 | Meisner et al. | 424/177 |
| 4,622,392 | 11/1986 | Hong et al. | 424/180 |
| 4,684,524 | 8/1987 | Eckenhoff et al. | 424/469 |
| 4,698,264 | 10/1987 | Steinke | 428/402.2 |
| 4,717,566 | 1/1988 | Eckenhoff et al. | 424/438 |
| 4,744,976 | 5/1988 | Snipes et al. | 424/408 |
| 4,772,471 | 9/1988 | Vanlerberghe et al. | 424/450 |
| 4,797,288 | 1/1989 | Sharma et al. | 424/476 |
| 4,840,799 | 6/1989 | Appelgren et al. | 424/493 |
| 4,849,405 | 7/1989 | Ecanow | 514/3 |
| 4,935,246 | 6/1990 | Ahrens | 424/480 |
| 4,963,367 | 10/1990 | Ecanow | 424/485 |
| 5,013,556 | 5/1991 | Woodle et al. | 424/450 |
| 5,055,300 | 10/1991 | Gupta | 424/409 |
| 5,055,304 | 10/1991 | Makino et al. | 424/465 |
| 5,093,198 | 3/1992 | Speaker et al. | 428/402.21 |

FOREIGN PATENT DOCUMENTS

WO 93/01802  2/1993  WIPO.

OTHER PUBLICATIONS

Conradi, R.A., et al., "The Influence of Peptide Structure on Transport Across Caco–2 Cells," Pharm. Res., 1991, 8 (12): pp. 1453–1459.

Boccu, E. et al., "Pharmocokinetic Properties of Polyethylene Glycol Derivatized Superoxide Dismutase," Pharm. Res. Comm., 1982, 14: PP. 11–120.

Igarashi, R. et al., "Biologically Active Peptides Conjugated with Lecithin for DDS" Proceed. Intern. Symp. Cont. Rel. Bioactiv. Mater. 1990, 17: pp. 367–368.

Taniguchi, T. et al., "Synthesis of Acyloyl Lysozyme and Improvement of its Lymphatic Transport Following Small Intestinal Administration in Rats," Proceed. Intern. Symp. Control. Rel. Bioactiv. Mater., 1992, 19: pp. 104–105.

Russell–Jones, G. J., "Vitamin B12 Drug Delivery," Proceed. Intern. Symp. Control. Rel. Bioactive. Mater., 1992, 19: pp. 102–103.

Baudys, M. et al., "Synthesis and Characteristics of Different Glycosylated Derivatives of Insulin," Proceed. Intern. Symp. Cont. Rel. Bioactiv. Mater., 1992, 19: pp. 210–211.

Chien, Y. W., Novel Drug Delivery Systems, pp. 678–679, Marcell Deffer, Inc., New York, NY, 1992.

Santiago, N. et al., "Oral Immunization of Rats with Influenze Virus M Protein (M1) Microspheres," Proceed. Intern. Symp. Cont. Rel. Bioactiv. Mater., 1992, 19: pp. 116–117.

Banting, R. G., et al., "Pancreatic Extracts in the Treatment of Diabetes Mellitus," The Canadian Med. Assoc. J. 1992, 12: pp. 141–146.

Brange, J. et al., "Chemical Stability of Insulin. 1. Hydrolytic Degradation During Storage of Pharmaceutical Preparations," Pharm. Res., 1992, 9 (6): pp. 715–726.

Nucci, et al., "The Therapeutic Value of Poly(ethylene glycol)—Modified Proteins," Ac. Drug. Del. Rev. 1991, 6: pp. 133–151.

(List continued on next page.)

*Primary Examiner*—Edward J. Cain
*Attorney, Agent, or Firm*—Steven J. Hultquist

[57] ABSTRACT

A stabilized conjugated therapeutic agent complex comprising a therapeutic agent conjugatively coupled to a polymer including lipophilic and hydrophilic moieties, wherein the therapeutic agent may for example be selected from the group consisting of insulin, calcitonin, ACTH, glucagon, somatostatin, somatotropin, somatomedin, parathyroid hormone, erythropoietin, hypothalamic releasing factors, prolactin, thyroid stimulating hormones, endorphins, enkephalins, vasopressin, non-naturally occurring opioids, superoxide dismutase, interferon, asparaginase, arginase, arginine deaminease, adenosine deaminase, ribonuclease, trypsin, chymotrypsin, papain, Ara-A (Arabinofuranosyladenine), Acylguanosine, Nordeoxyguanosine, Azidothymidine, Dideoxyadenosine, Dideoxycytidine, Dideoxyinosine Floxuridine, 6-Mercaptopurine, Doxorubicin, Daunorubicin, or I-darubicin, Erythormycin, Vancomycin, oleandomycin, Ampicillin; Quinidine and Heparin. In a particular aspect, the invention comprises an insulin composition suitable for parenteral as well as non-parenteral administration, preferably oral or parenteral administration, comprising insulin covalently coupled with a polymer including (i) a linear polyalkylene glycol moiety and (ii) a lipophilic moiety, wherein the insulin, the linear polyalkylene glycol moiety and the lipophilic moiety are conformationally arranged in relation to one another such that the insulin in the composition has an enhanced in vivo resistance to enzymatic degradation, relative to insulin alone. One, two, or three polymer constituents may be covalently attached to the therapeutic agent molecule, with one polymer constituent being preferred. The conjugates of the invention are usefully employed in therapeutic as well as non-therapeutic, e.g., diagnostic, applications, and the therapeutic agent and polymer may be covalently coupled to one another, or alternatively may be associatively coupled to one another, e.g., by hydrogen bonding or other associative bonding relationship.

44 Claims, 2 Drawing Sheets

OTHER PUBLICATIONS

Brange, J. et al., "Chemical Stability of Insulin. 2. Formation of Higher Molecular Weight Transformation Products During Storage of Pharmaceutical Preparations," Pharm. Res., 1992, 9 (6): pp. 727–734.

Robbins, D.C. et al., "Antibodies to Covalent Aggregates of Insulin in Blood of Insulin–Using Diabetic Patients," Diabetes, 1987, 36: pp. 838–841.

Maislos, M. et al., "The Source of the Circulating Aggregate of Insulin in Type I Diabetic Patients is Therapeutic Insulin," J. Clin. Invest., 1986, 77: pp. 717–723.

Ratner, R. E. et al., "Persistent Cutaneous Insulin Allergy Resulting from High–Molecular Weight Insulin Aggregates," Diabetes, 1990, 39: pp. 728–733.

Oka, K. et al., "Enhanced Intestinal Absorption of a Hydrophobic Polymer–Conjugated Protein Drug, Smancs, in an Oily Formulation," Pharm. Res., 1990, 7 (8): pp. 852–855.

Saffran, M. et al., "A New Approach to the Oral Administration of Insulin and Other Peptide Drugs," Science, 1986, 233: pp. 1081–1084.

Abuschowski, A. and F. F. Davis, "Soluble Polymer–Enzyme Adducts," pp. 368–383, Enzymes as Drugs, J.S. Holcenberg, John Wiley, 1981.

Akiyama, M. et al., "The Synthesis of New Derivatives of 1–$\beta$–D–Arabinofuranosylcytosine," Chem. Pharm. Bull., 1978, 26(3): p. 981.

Gish, D. T. et al., "Nucleic Acids. 11. Synthesis of 5'–Esters of 1–$\beta$–D–Arabinofuranosylcytosine Possessing Antileukemic and Immunosuppressive Activity," J. Med. Chem., 1971, 14(12): pp. 1159–1162.

Baker, D.C. et al., "Prodrugs of 9–$\beta$–D–Arabinofuranosyladenine. 1. Synthesis and Evaluation of Some 5'–(O–Acyl) Derivatives," J. Med. Chem., 1978, 21(12): pp. 1218–1221.

Hostetler, K. Y. et al., "Synthesis and Antiretroviral Activity of Phospholipid Analogs of Azidothymidine and Other Antiviral Nucleosides," The Journal of Biological Chemistry, 1990, 265(11): pp. 6112–6117.

Hong, C. I. et al., "Nucleoside Conjugates. 7. Synthesis and Antitumor Avtivity of 1–$\beta$–D–Arabinofuranosylcytosine Conjugates of Ether Lipids," J. Med. Chem., 1986, 29: pp. 2038–2044.

Aoshima, M. et al., "$N^4$–Behenoyl–1–$\beta$–D– Arabinofuranofuranosylcytosine as a Potential New Antitumor Agent," Cancer Research, 1977, 37: pp. 2481–2486.

Zalipsky, S. et al., "Attachment of Drugs to Polyethylene Glycols," Eur. Polym. J., 1983, 19(12): pp. 1177–1183.

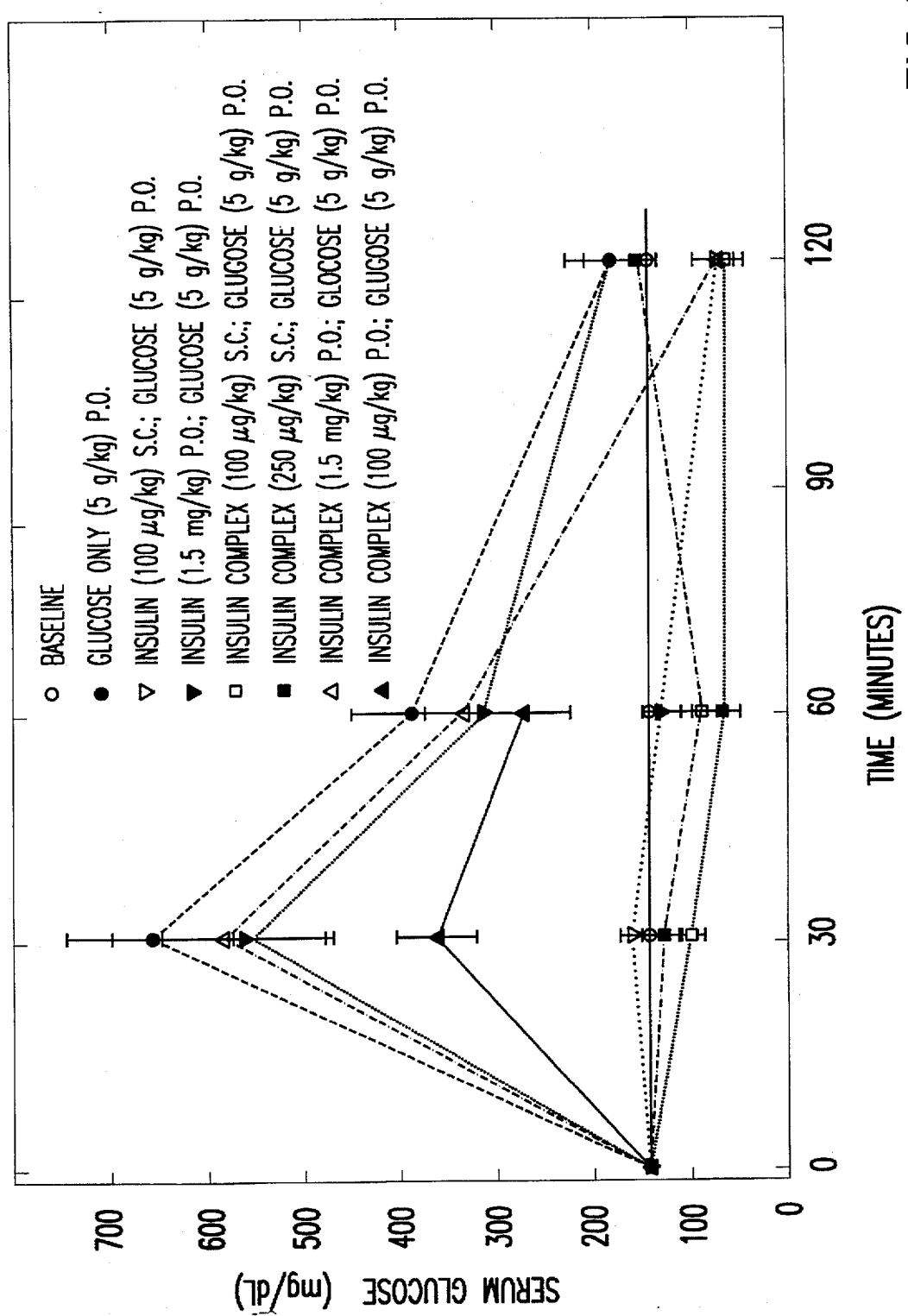

CONJUGATION-STABILIZED THERAPEUTIC AGENT COMPOSITIONS, DELIVERY AND DIAGNOSTIC FORMULATIONS COMPRISING SAME, AND METHOD OF MAKING AND USING THE SAME

CROSS-REFERENCE TO RELATED APPLICATIONS

This is a continuation-in-part of U.S. application Ser. No. 08/276,890 filed Jul. 19, 1994 and issuing Aug. 1, 1995 as U.S. Pat. No. 5,438,040, which in turn is a division of U.S. application Ser. No. 08/059,701 filed May 10, 1993 and issued Oct. 25, 1994 as U.S. Pat. No. 5,359,030.

BACKGROUND OF THE INVENTION

1. Field of the Invention

The present invention relates to conjugation-stabilized compositions and formulations of therapeutic agents, and to methods of making and using same. The compositions of the invention may comprise therapeutic agents such as proteins, peptides, nucleosides, nucleotides, antiviral agents, antineoplastic agents, antibiotics, antiarrhythmics, anticoagulants, etc., and prodrugs precursors, derivatives, and intermediates thereof.

2. Description of the Related Art

In the field of pharmaceutical therapeutic intervention, and the treatment of disease states and physiological conditions, a wide variety of therapeutic agents have come into use, including various proteins, peptides, nucleosides, nucleotides, antiviral agents, antineoplastic agents, antibiotics, antiarrhythmics, anti-coagulants, etc., and prodrugs precursors, derivatives, and intermediates of the foregoing.

For example, the use of polypeptides and proteins for the systemic treatment of specific diseases is now well accepted in medical practice. The role that the peptides play in replacement therapy is so important that many research activities are being directed towards the synthesis of large quantities by recombinant DNA technology. Many of these polypeptides are endogenous molecules which are very potent and specific in eliciting their biological actions. Other non-(poly)peptidyl therapeutic agents are equally important and pharmaceutically efficacious.

A major factor limiting the usefulness of these therapeutic substances for their intended application is that they are easily metabolized by plasma proteases when given parenterally. The oral route of administration of these substances is even more problematic because in addition to proteolysis in the stomach, the high acidity of the stomach destroys them before they reach their intended target tissue. For example, polypeptides and protein fragments, produced by the action of gastric and pancreatic enzymes, are cleaved by exo and endopeptidases in the intestinal brush border membrane to yield di- and tripeptides, and even if proteolysis by pancreatic enzymes is avoided, polypeptides are subject to degradation by brush border peptidases. Any of the therapeutic agent that survives passage through the stomach is further subjected to metabolism in the intestinal mucosa where a penetration barrier prevents entry into the cells.

In spite of these obstacles, there is substantial evidence in the literature to suggest that nutritional and pharmaceutical therapeutic agents such as proteins are absorbed through the intestinal mucosa. On the other hand, nutritional and drug (poly)peptides are absorbed by specific peptide transporters in the intestinal mucosa cells. These findings indicate that properly formulated therapeutic agents such as (poly) peptides and proteins may be administered by the oral route, with retention of sufficient biological activity for their intended use. If, however, it were possible to modify these therapeutic agents so that their physiological activities were maintained totally, or at least to a significant degree, and at the same time stabilize them against proteolytic enzymes and enhance their penetration capability through the intestinal mucosa, then it would be possible to utilize them properly for their intended purpose. The product so obtained would offer advantages in that more efficient absorption would result, with the concomitant ability to use lower doses to elicit the optimum therapeutic effect.

The problems associated with oral or parenteral administration of therapeutic agents such as proteins are well known in the pharmaceutical industry, and various strategies are being used in attempts to solve them. These strategies include incorporation of penetration enhancers, such as the salicylates, lipid-bile salt-mixed micelles, glycerides, and acylcarnitines, but these frequently are found to cause serious local toxicity problems, such as local irritation and toxicity, complete abrasion of the epithelial layer and inflammation of tissue. These problems arise because enhancers are usually co-administered with the therapeutic agent and leakages from the dosage form often occur. Other strategies to improve oral delivery include mixing the therapeutic agent with protease inhibitors, such as aprotinin, soybean trypsin inhibitor, and amastatin, in an attempt to limit degradation of the administered therapeutic agent. Unfortunately these protease inhibitors are not selective, and endogenous proteins are also inhibited. This effect is undesirable.

Enhanced penetration of therapeutic agents across mucosal membranes has also been pursued by modifying the physicochemical properties of candidate drugs. Results indicate that simply raising lipophilicity is not sufficient to increase paracellular transport. Indeed it has been suggested that cleaving peptide-water hydrogen bonds is the main energy barrier to overcome in obtaining diffusion of peptide therapeutics across membranes (Conradi, R. A., Hilgers, A. R., Ho, N. F. H., and Burton, P. S., "The influence of peptide structure on transport across Caco-2 cells", Pharm. Res., 8, 1453–1460, (1991)). Protein stabilization has been described by several authors. Abuchowski and Davis ("Soluble polymers-Enzyme adducts", In: Enzymes as Drugs, Eds. Holcenberg and Roberts, J. Wiley and Sons, New York, N.Y., (1981)) disclosed various methods of derivatization of enzymes to provide water soluble, non-immunogenic, in vivo stabilized products.

A great deal of work dealing with protein stabilization has been published. Abuchowski and Davis disclose various ways of conjugating enzymes with polymeric materials (Ibid.). More specifically, these polymers are dextrans, polyvinyl pyrrolidones, glycopeptides, polyethylene glycol and polyamino acids. The resulting conjugated polypeptides are reported to retain their biological activities and solubility in water for parenteral applications. The same authors, in U.S. Pat. No. 4,179,337, disclose that polyethylene glycol rendered proteins soluble and non-immunogenic when coupled to such proteins. These polymeric materials, however, did not contain fragments suited for intestinal mucosa binding, nor did they contain any moieties that would facilitate or enhance membrane penetration. While these conjugates were water-soluble, they were not intended for oral administration.

Meisner et al., U.S. Pat. No. 4,585,754, teaches that proteins may be stabilized by conjugating them with chondroitin sulfates. Products of this combination are usually polyanionic, very hydrophilic, and lack cell penetration capability. They are usually not intended for oral administration.

Mill et al., U.S. Pat. No. 4,003,792, teaches that certain acidic polysaccharides, such as pectin, algesic acid, hyaluronic acid and carrageenan, can be coupled to proteins to produce both soluble and insoluble products. Such polysaccharides are polyanionic, derived from food plants. They lack cell penetration capability and are usually not intended for oral administration.

In Pharmacological Research Communication 14, 11–120 (1982), Boccu et al. disclosed that polyethylene glycol could be linked to a protein such as superoxide dismutase ("SOD"). The resulting conjugated product showed increased stability against denaturation and enzymatic digestion. The polymers did not contain moieties that are necessary for membrane interaction and thus suffer from the same problems as noted above in that they are not suitable for oral administration.

Other techniques of stabilizing peptide and protein drugs in which proteinaceous drug substances are conjugated with relatively low molecular weight compounds such as aminolethicin, fatty acids, vitamin $B_{12}$, and glycosides, are described in the following articles: R. Igarishi et al., "Proceed. Intern. Symp. Control. Rel. Bioact. Materials, 17, 366, (1990); T. Taniguchi et al. Ibid 19, 104, (1992); G. J. Russel-Jones, Ibid, 19, 102, (1992); M. Baudys et al., Ibid, 19, 210, (1992). The modifying compounds are not polymers and accordingly do not contain moieties necessary to impart both the solubility and membrane affinity necessary for bioavailability following oral as well as parenteral administration. Many of these preparations lack oral bioavailability.

Another approach which has been taken to lengthen the in vivo duration of action of proteinaceous substances is the technique of encapsulation. M. Saffan et al., in Science, 223, 1081, (1986) teaches the encapsulation of proteinaceous drugs in an azopolymer film for oral administration. The film is reported to survive digestion in the stomach but is degraded by microflora in the large intestine, where the encapsulated protein is released. The technique utilizes a physical mixture and does not facilitate the absorption of released protein across the membrane.

Ecanow, U.S. Pat. No. 4,963,367, teaches that physiologically active compounds, including proteins, can be encapsulated by a coacervative-derived film and the finished product can be suitable for transmucosal administration. Other formulations of the same invention may be administered by inhalation, oral, parenteral and transdermal routes. These approaches do not provide intact stability against acidity and proteolytic enzymes of the gastrointestinal tract, the property as desired for oral delivery.

Another approach taken to stabilize protein drugs for oral as well as parenteral administration involves entrapment of the therapeutic agent in liposomes. A review of this technique is found in Y. W. Chien, "New Drug Delivery Systems", Marcel Dekker, New York, N.Y., 1992. Liposome-protein complexes are physical mixtures; their administration gives erratic and unpredictable results. Undesirable accumulation of the protein component in certain organs has been reported, in the use of such liposome-protein complexes. In addition to these factors, there are additional drawbacks associated with the use of liposomes, such as cost, difficult manufacturing processes requiring complex lyophilization cycles, and solvent incompatibilities. Moreover, altered biodistribution and antigenicity issues have been raised as limiting factors in the development of clinically useful liposomal formulations.

The use of "proteinolds" has been described recently (Santiago, N., Milstein, S. J., Rivera, T., Garcia, E., Chang., T. C., Baughman, R. A., and Bucher, D., "Oral Immunization of Rats with Influenza Virus M Protein (M1) Microspheres", Abstract #A 221, Proc. Int. Symp. Control. Rel. Bioac. Mater.,19, 116 (1992)). Oral delivery of several classes of therapeutics has been reported using this system, which encapsulates the drug of interest in a polymeric sheath composed of highly branched amino acids. As is the case with liposomes, the drugs are not chemically bound to the proteinold sphere, and leakage of drug out of the dosage form components is possible.

A peptide which has been the focus of much synthesis work, and efforts to improve its administration and bioassimilation, is insulin.

The use of insulin as a treatment for diabetes dates back to 1922, when Banting et al. ("Pancreatic Extracts in the Treatment of Diabetes Mellitus," Can. Med. Assoc. J., 12, 141–146 (1922)) showed that the active extract from the pancreas had therapeutic effects in diabetic dogs. Treatment of a diabetic patient in that same year with pancreatic extracts resulted in a dramatic, life-saving clinical improvement. A course of daily injections of insulin is required for extended recovery.

The insulin molecule consists of two chains of amino acids linked by disulfide bonds; the molecular weight of insulin is around 6,000. The β-cells of the pancreatic islets secrete a single chain precursor of insulin, known as proinsulin. Proteolysis of proinsulin results in removal of four basic amino acids (numbers 31, 32, 64 and 65 in the proinsulin chain: Arg, Arg, Lys, Arg respectively) and the connecting ("C") peptide. In the resulting two-chain insulin molecule, the A chain has glycine at the amino terminus, and the B chain has phenylalanine at the amino terminus.

Insulin may exist as a monomer, dimer or a hexamer formed from three of the dimers. The hexamer is coordinated with two $Zn^{2+}$ atoms. Biological activity resides in the monomer. Although until recently bovine and porcine insulin were used almost exclusively to treat diabetes in humans, numerous variations in insulin between species are known. Porcine insulin is most similar to human insulin, from which it differs only in having an alanine rather than threonine residue at the B-chain C-terminus. Despite these differences most mammalian insulin has comparable specific activity. Until recently animal extracts provided all insulin used for treatment of the disease. The advent of recombinant technology allows commercial scale manufacture of human insulin (e.g., Humulin™ insulin, commercially available from Eli Lilly and Company, Indianapolis, Ind.).

Although insulin has now been used for more than 70 years as a treatment diabetes, few studies of its formulation stability appeared until two recent publications (Brange, J., Langkjaer, L., Havelund, S., and Volund, A., "Chemical stability of insulin. I. Degradation during storage of pharmaceutical preparations," Pharm. Res., 9, 715–726, (1992); and Brange, J. Havelund, S., and Hougaard, P., "Chemical stability of insulin. 2. Formulation of higher molecular weight transformation products during storage of pharmaceutical preparations," Pharm. Res., 9, 727–734, (1992)). In these publications, the authors exhaustively describe chemical stability of several insulin preparations under varied temperature and pH conditions. Earlier reports focused almost entirely on biological potency as a measure of insulin formulation stability. However the advent of several new and powerful analytical techniques—disc electrophoresis, size exclusion chromatography, and HPLC—allows a detailed examination of insulin's chemical stability profile. Early chemical studies on insulin stability were difficult because the recrystallized insulin under examination was found to be no more than 80–90% pure. More recently monocomponent, high-purity insulin has become available. This monocomponent insulin contains impurities at levels undetectable by current analysis techniques.

Formulated insulin is prone to numerous types of degradation. Nonenzymatic deamidiation occurs when a side-chain amide group from a glutaminyl or asparaginyl residue is hydrolyzed to a free carboxylic acid. There are six possible sites for such deamidiation in insulin: $Gln^{A5}$, $Gln^{A15}$, $Asn^{A18}$, $Asn^{A21}$, $Asn^{B3}$, and $Gln^{B4}$. Published reports suggest that the three Asn residues are most susceptible to such reactions.

Brange et al. (ibid) reported that in acidic conditions insulin is rapidly degraded by extensive deamidation at $Asn^{A21}$. In contrast, in neutral formulations deamidation takes place at $Asn^{B3}$ at a much slower rate, independent of insulin concentration and species of origin of the insulin. However, temperature and formulation type play an important role in determining the rate of hydrolysis at B3. For example, hydrolysis at B3 is minimal if the insulin is crystalline as opposed to amorphous. Apparently the reduced flexibility (tertiary structure) in the crystalline form slows the reaction rate. Stabilizing the tertiary structure by incorporating phenol into neutral formulations results in reduced rates of deamidation.

In addition to hydrolytic degradation products in insulin formulations, high molecular weight transformation products are also formed. Brange et al. showed by size exclusion chromatography that the main products formed on storage of insulin formulations between 4° and 45° C. are covalent insulin dimers. In formulations containing protamine, covalent insulin protamine products are also formed. The rate of formulation of insulin-dimer and insulin-protamine products is affected significantly by temperature. For human or porcine insulin, (regular N1 preparation) time to formation of 1% high molecular weight products is decreased from 154 months to 1.7 months at 37° C. compared to 4° C. For zinc suspension preparations of porcine insulin, the same transformation would require 357 months at 4° C. but only 0.6 months at 37° C.

These types of degradation in insulin may be of great significance to diabetic subjects. Although the formation of high molecular weight products is generally slower than the formation of hydrolytic (chemical) degradation products described earlier, the implications may be more serious. There is significant evidence that the incidence of immunological responses to insulin may result from the presence of covalent aggregates of insulin (Robbins, D. C. Cooper, S. M. Fineberg, S. E., and Mead, P. M., "Antibodies to covalent aggregates of insulin in blood of insulin-using diabetic patients", Diabetes, 36, 838–841, (1987); Maislos, M., Mead, P. M., Gaynor, D. H., and Robbins, D. C., "The source of the circulating aggregate of insulin in type I diabetic patients is therapeutic insulin", *J. Clin. Invest.*, 77, 717–723. (1986); and Ratner R. E., Phillips, T. M., and Steiner, M., "Persistent cutaneous insulin allergy resulting from high molecular weight insulin aggregates", *Diabetes*, 39, 728–733, (1990)). As many as 30% of diabetic subjects receiving insulin show specific antibodies to covalent insulin dimers. At a level as low as 2% it was reported that the presence of covalent insulin dimers generated a highly significant response in lymphocyte stimulation in allergic patients. Responses were not significant when dimer content was in the range 0.3–0.6%. As a result it is recommended that the level of covalent insulin dimers present in formulation be kept below 1% to avoid clinical manifestations.

Several insulin formulations are commercially available; although stability has been improved to the extent that it is no longer necessary to refrigerate all formulations, there remains a need for insulin formulations with enhanced stability. A modified insulin which is not prone to formation of high molecular weight products would be a substantial advance in the pharmaceutical and medical arts, and modifications providing this stability (and in addition providing the possibility of oral availability of insulin) would make a significant contribution to the management of diabetes.

In addition to the in vivo usage of therapeutic agents, polypeptides, proteins, nucleosides, and other molecules which are bioactive in vivo, also find substantial and increasing use in diagnostic reagent applications. In many such applications, these agents are utilized in solution environments wherein they are susceptible to thermal and enzymic degradation. Examples of such diagnostic agents include enzymes, peptide and protein hormones, antibodies, enzyme-protein conjugates used for immunoassay, antibody-hapten conjugates, viral proteins such as those used in a large number of assay methodologies for the diagnosis or screening of diseases such as AIDS, hepatitis, and rubella, peptide and protein growth factors used for example in tissue culture, enzymes used in clinical chemistry, and insoluble enzymes such as those used in the food industry. As a further specific example, alkaline phosphatase is widely utilized as a reagent in kits used for the colorimetric detection of antibody or antigen in biological fluids. Although such enzyme is commercially available in various forms, including free enzyme and antibody conjugates, its storage stability and solution often is limited. As a result, alkaline phosphatase conjugates are frequently freeze-dried, and additives such as bovine serum albumin and Tween 20 are used to extend the stability of the enzyme preparations. Such approaches, while advantageous in some instances to enhance the resistance to degradation of the therapeutic and/or diagnostic agents, have various shortcomings which limit their general applicability.

SUMMARY OF THE INVENTION

The present invention relates generally to conjugation-stabilized therapeutic and/or diagnostic agent compositions and formulations, and to methods of making and using same.

More particularly, the present invention relates in one broad compositional aspect to covalently conjugated therapeutic and/or diagnostic complexes wherein the therapeutic and/or diagnostic agent peptide is covalently bonded to one or more molecules of a polymer incorporating as an integral part thereof a hydrophilic moiety, e.g., a linear polyalkylene glycol, and wherein said polymer incorporates a lipophilic moiety as an integral part thereof.

In one particular aspect, the present invention relates to a physiologically active therapeutic agent composition comprising a physiologically active therapeutic agent covalently coupled with a polymer comprising (i) a linear polyalkylene glycol moiety and (ii) a lipophilic moiety, wherein the therapeutic agent, linear polyalkylene glycol moiety, and the lipophilic moiety are conformationally arranged in relation to one another such that the physiologically active therapeutic agent in the physiologically active therapeutic agent composition has an enhanced in vivo resistance to enzymatic degradation, relative to the physiologically active therapeutic agent alone (i.e., in an unconjugated form devoid of the polymer coupled thereto).

In another aspect, the invention relates to a physiologically active therapeutic agent composition of three-dimensional conformation comprising a physiologically active therapeutic agent covalently coupled with a polysorbate complex comprising (i) a linear polyalkylene glycol moiety and (ii) a lipophilic moiety, wherein the physiologically active therapeutic agent, the linear polyalkylene glycol moiety and the lipophilic moiety are conformationally arranged in relation to one another such that (a) the lipophilic moiety is exteriorly available in the three-dimensional conformation, and (b) the physiologically active therapeutic agent in the physiologically active therapeutic agent composition has an enhanced in vivo resistance to enzymatic degradation, relative to the physiologically active therapeutic agent alone.

In a further aspect, the invention relates to a multiligand conjugated therapeutic agent complex comprising a triglyceride backbone moiety, having:

a bioactive therapeutic agent covalently coupled with the triglyceride backbone moiety through a polyalkylene glycol spacer group bonded at a carbon atom of the triglyceride backbone moiety; and at least one fatty acid moiety covalently attached either directly to a carbon atom of the triglyceride backbone moiety or covalently joined through a polyalkylene glycol spacer moiety.

In such multiligand conjugated therapeutic agent complex, the α' and β carbon atoms of the triglyceride bioactive moiety may have fatty acid moieties attached by covalently bonding either directly thereto, or indirectly covalently bonded thereto through polyalkylene glycol spacer moieties. Alternatively, a fatty acid moiety may be covalently attached either directly or through a polyalkylene glycol spacer moiety to the α and α' carbons of the triglyceride backbone moiety, with the bioactive therapeutic agent being covalently coupled with the γ-carbon of the triglyceride backbone moiety, either being directly covalently bonded thereto or indirectly bonded thereto through a polyalkylene spacer moiety. It will be recognized that a wide variety of structural, compositional, and conformational forms are possible for the multiligand conjugated therapeutic agent complex comprising the triglyceride backbone moiety, within the scope of the foregoing discussion.

In such a multiligand conjugated therapeutic agent complex, the bioactive therapeutic agent may advantageously be covalently coupled with the triglyceride modified backbone moiety through alkyl spacer groups, or alternatively other acceptable spacer groups, within the broad scope of the invention. As used in such context, acceptability of the spacer group refers to steric, compositional, and end use application specific acceptability characteristics.

In yet another aspect, the invention relates to a polysorbate complex comprising a polysorbate moiety including a triglyceride backbone having covalently coupled to α,α' and β carbon atoms thereof functionalizing groups including:

(i) a fatty acid group; and (ii) a polyethylene glycol group having a physiologically active moiety covalently bonded thereto, e.g., a physiologically active moiety is covalently bonded to an appropriate functionality of the polyethylene glycol group.

Such covalent bonding may be either direct, e.g., to a hydroxy terminal functionality of the polyethylene glycol group, or alternatively, the covalent bonding may be indirect, e.g., by reactively capping the hydroxy terminus of the polyethylene glycol group with a terminal carboxy functionality spacer group, so that the resulting capped polyethylene glycol group has a terminal carboxy functionality to which the physiologically active moiety may be covalently bonded.

The invention relates to a further aspect to a stable, aqueously soluble, conjugated therapeutic agent complex comprising a physiologically active therapeutic agent covalently coupled to a physiologically compatible polyethylene glycol modified glycolipid moiety. In such complex, the physiologically active therapeutic agent may be covalently coupled to the physiologically compatible polyethylene glycol modified glycolipid moiety by a lablie covalent bond at a free amino acid group of the therapeutic agent, wherein the lablie covalent bond is scissionable in vivo by biochemical hydrolysis and/or proteolysis. The physiologically compatible polyethylene glycol modified glycolipid moiety may advantageously comprise a polysorbate polymer, e.g., a polysorbate polymer comprising fatty acid ester groups selected from the group consisting of monopalmitate, dipalmitate, monolaurate, dilaurate, trilaurate, monoleate, dioleate, trioleate, monostearate, distearate, and tristearate. In such complex, the physiologically compatible polyethylene glycol modified glycolipid moiety may suitably comprise a polymer selected from the group consisting of polyethylene glycol ethers of fatty acids, and polyethylene glycol esters of fatty acids, wherein the fatty acids for example comprise a fatty acid selected from the group consisting of lauric, palmitic, oleic, and stearic acids.

In the above complex, the physiologically active therapeutic agent may by way of illustration comprise a peptide, protein, nucleoside, nucleotide, antineoplastic, agent, antibiotic, anticoagulant, antiarrhythmic agent, antiviral agent, or prodrugs, precursors, intermediates, or derivatives thereof.

For example, the therapeutic agent may comprise peptide selected from the group consisting of insulin, calcitonin, ACTH, glucagon, somatostatin, somatotropin, somatomedin, parathyroid hormone, erythropoietin, hypothalmic releasing factors, prolactin, thyroid stimulating hormones, endorphins, enkephalins, vasopressin, non-naturally occurring opiods, superoxide dismutase, interferon, asparaginase, arginase, arginine deaminease, adenosine deaminase ribonuclease, trypsin, chemotrypsin, and papain.

As other examples, the therapeutic agent may comprise: An antiviral such as: Ara-A (Arabinofuranosyladenine), Acylguanosine, Nordeoxyguanosine, Azidothymidine, Dideoxyadenosine, or Dideoxycytidine; an anti-cancer agent such as Dideoxyinosine Floxuridine, 6-Mercaptopurine, Doxorubicin, Daunorubicin, or I-darubicin; and antibiotic such as Erythormycin, Vancomycin, oleandomycin, or Ampicillin; an antiarrhythmic such as Quinidine; or an anticoagulant such as Heparins.

In another aspect, the present invention relates to an oral administration dosage form for the mediation of insulin deficiency, comprising a pharmaceutically acceptable carrier and a stable, aqueously soluble, conjugated insulin complex comprising insulin or proinsulin covalently coupled to a physiologically compatible polyethylene glycol modified glycolipid moiety.

In a further aspect, the invention relates to a method of treating insulin deficiency in a human or non-human mammalian subject exhibiting such deficiency, comprising orally administering to the subject an effective amount of a conjugated insulin composition comprising a stable, aqueously soluble, conjugated insulin complex comprising insulin covalently or proinsulin covalently coupled to a physiologically compatible polyethylene glycol modified glycolipid moiety.

The term "peptide" as used herein is intended to be broadly construed as inclusive of polypeptides per se having molecular weights of up to 10,000, as well as proteins having molecular weights of greate molecular weights are number average molecular weights. As used herein, the term "covalently coupled" means that the specified moieties are either directly covalently bonded to one another, or else are indirectly covalently joined to one another through an intervening moiety or moieties, such as a bridge, spacer, or linkage moiety or moieties. The term "conjugatively coupled" means that the specified moieties are either covalently coupled to one another or they are non-covalently coupled to one another, e.g., by hydrogen bonding, ionic bonding, Van der Waals forces, etc. The term "therapeutic agent" means an agent which is therapeutically useful, e.g., an agent for the treatment, remission or attenuation of a disease state, physiological condition, symptoms, or etiological factors, or for the evaluation or diagnosis thereof.

The invention thus comprehends various compositions for therapeutic (in vivo) application, wherein the therapeutic agent component of the conjugated therapeutic agent complex is a physiologically active, or bioactive, therapeutic agent. In such therapeutic agent-containing compositions, the conjugation of the therapeutic agent component to the polymer comprising hydrophilic and lipophilic moieties may be direct covalent bonding or indirect (through appropriate spacer groups) bonding, and the hydrophilic and lipophilic moieties may also be structurally arranged in the polymeric conjugating structure in any suitable manner involving direct or indirect covalent bonding, relative to one another. Thus, a wide variety of therapeutic agent species may be accommodated in the broad practice of the present invention, as necessary or desirable in a given end use therapeutic application.

In another aspect, covalently coupled therapeutic agent compositions such as those described above may utilize therapeutic agent components intended for diagnostic or in vitro applications, wherein the therapeutic agent is for example a diagnostic reagent, or a complement of a diagnostic conjugate for immunoassay or other diagnostic or non-in vivo applications. In such non-therapeutic applications, the complexes of the invention are highly usefully employed as stabilized compositions which may for example be formulated in compatible solvents or other solution-based formulations to provide stable compositional forms which are of enhanced resistance to degradation.

In the foregoing therapeutic and non-therapeutic (e.g., diagnostic) applications, the present invention relates in a broad compositional aspect to covalently conjugated therapeutic agent complexes wherein the therapeutic agent is covalently bonded to one or more molecules of a polymer incorporating as an integral part of said polymer a hydrophilic moiety, e.g., a polyalkylene glycol moiety, and a lipophilic moiety, e.g., a fatty acid moiety. In one preferred aspect, the therapeutic agent may be covalently conjugated by covalent bonding with one or more molecules of a linear polyalkylene glycol polymer incorporated in which, as an integral part thereof is a lipophilic moiety, e.g., a fatty acid moiety.

In another particular broad aspect, the present invention relates to non-covalently conjugated therapeutic agent complexes wherein the therapeutic agent is non-covalently associated with one or more molecules of a polymer incorporating as an integral part thereof a hydrophilic moiety, e.g., a polyalkylene glycol moiety, and a lipophilic moiety, e.g., a fatty acid moiety. The polymer may be variously structured and arranged analogous to description of the polymer in the covalently conjugated therapeutic agent complexes described above, but wherein the therapeutic agent is not bonded to the polymer molecule(s) in a covalent manner, but is nonetheless associated with the polymer, as for example by associative bonding, such as hydrogen bonding, ionic bonding or complexation, Van der Waals bonding, micellular encapsulation or association (of the specific therapeutic agent), etc.

Such non-covalent associations of a therapeutic agent component and polymeric moiety/(ies) may for example utilize a therapeutic agent component for therapeutic (e.g., in vivo ) applications, as well as non-therapeutic therapeutic agent components, e.g., for diagnostic or other (in vitro) use.

In such associatively conjugated therapeutic agent compositions, the polymer component may be suitably constructed, modified, or appropriately functionalized to impart the ability for associative conjugation in a selectively manner (for example, to impart hydrogen bonding capability to the polymer viz-a-vis the therapeutic agent), within the skill of the art.

Other aspects, features, and modifications of the invention will be more fully apparent from the ensuing disclosure and appended claims.

BRIEF DESCRIPTION OF THE DRAWINGS

FIG. 2 is a graph of serum glucose, in mg/dL, as a function of time, in hours, for administration of insulin in various forms.

DETAILED DESCRIPTION OF THE INVENTION, AND PREFERRED EMBODIMENTS THEREOF

Figure 1:
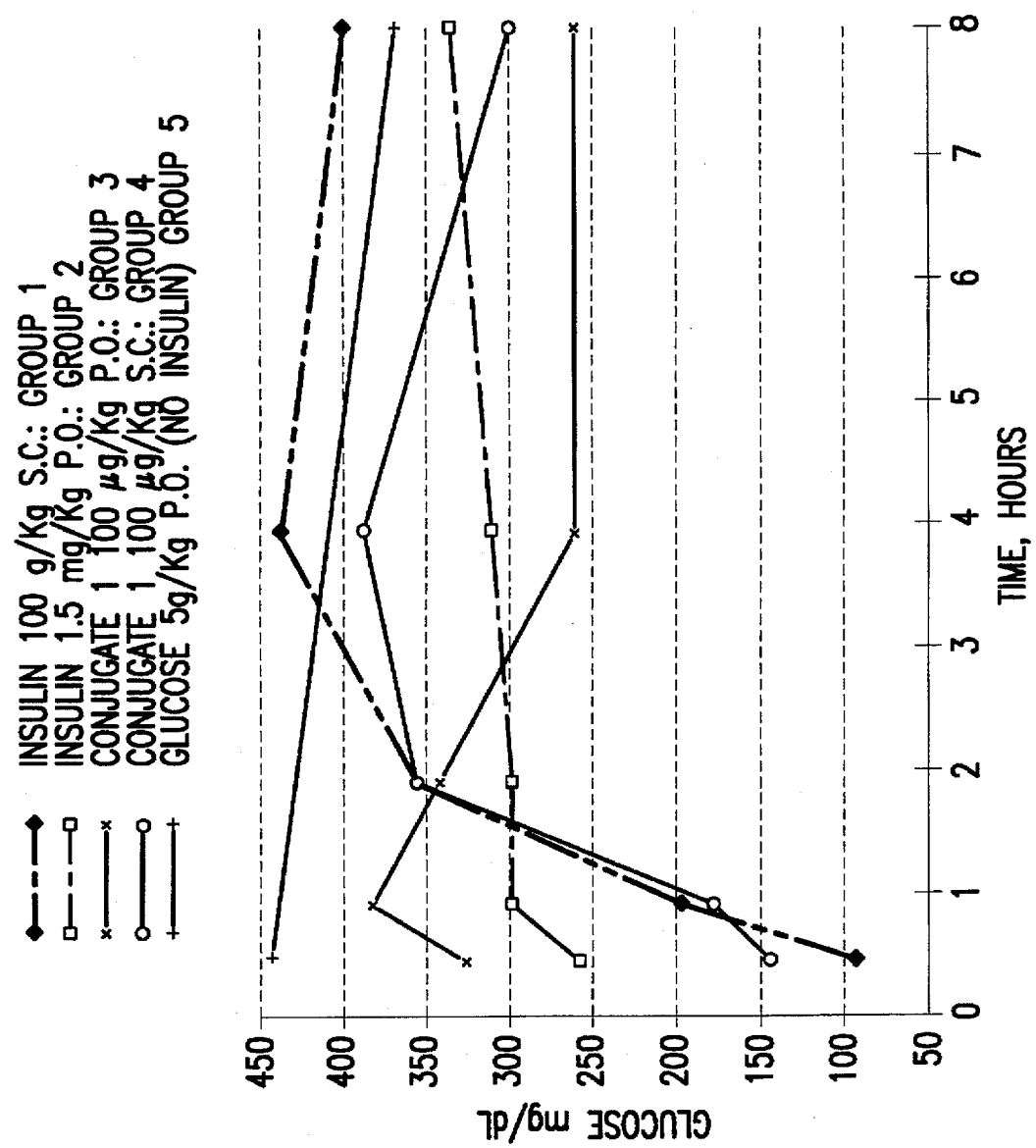
FIG. 1 is a graph of serum glucose, in mg/dL, as a function of time, in minutes, for administration of insulin per se and in complexed forms.

Modification of therapeutic agents with non-toxic, non-immunogenic polymers may offer certain advantages. If modifications are made in such a way that the products (polymer-therapeutic agent conjugates) retain all or most of their biological activities the following properties may result: epithelial penetration capability may be enhanced; the modified therapeutic agent may be protected from proteolytic digestion and subsequent abolition of activity; affinity for endogenous transport systems may be improved; chemical stability against stomach acidity may be imparted; the balance between lipophilicity and hydrophobicity of the polymers may be optimized. Proteinaceous substances endowed with the improved properties described above may be effective as replacement therapy following either oral or parenteral administration. Other routes of administration, such as nasal and transdermal, may also be possible using the modified therapeutic agent.

In non-therapeutic (e.g., diagnostic) applications, conjugation-stabilization of diagnostic and/or reagent species of peptides, nucleosides, or other therapeutic agents, including precursors and intermediates of end-use nucleosides, peptides or other products, provides corresponding advantages, when the conjugation component is covalently bonded to a polymer in the manner of the present invention. The resultingly covalently conjugated agent is resistant to environmental degradative factors, including solvent- or solution-mediated degradation processes. As a result of such enhanced resistance to degradation, the shelf life of the active ingredient is able to be significantly increased, with concomitant reliability of the therapeutic agent-containing composition in the specific end use for which same is employed.

The covalent conjugation of therapeutic agents with polymers in the manner of the present invention effectively minimizes hydrolytic degradation, and achieves in vitro and in vivo stabilization.

Analogous benefits are realized when therapeutic, diagnostic, or reagent species are non-covalently, associatively conjugated with polymer molecule(s) in the manner of the present invention.

Utilizing insulin covalently bonded to the polymer component as an illustrative embodiment of the invention, the nature of the conjugation, involving cleavable covalent chemical bonds, allows for control in terms of the time course over which the polymer may be cleaved from the peptide (insulin). This cleavage may occur by enzymatic or chemical mechanisms. The conjugated polymer-peptide complex will be intrinsically active. Full activity will be realized following enzymatic cleavage of the polymer from the peptide. Further, the chemical modification will allow penetration of the attached peptide, e.g., insulin, through cell membranes. In a preferred aspect of the present invention, membrane penetration-enhancing properties of lipophilic fatty acid residues are incorporated into the body of the conjugating polymer. In this respect, again utilizing insulin as the peptide of interest, fatty acid polymer derivatives of insulin improve the intestinal absorption of insulin: carbamylation of the amino groups of $Phe^{B1}$ and $Lys^{B29}$ with long-chain fatty acid polymers yield compounds which provide some degree of hypoglycemic activity. This derivatization increases the stability of insulin in intestinal mucosa and its absorption from the small intestine.

While the ensuing description is primarily and illustratively directed to the use of insulin as a peptide component in various compositions and formulations of the invention, it will be appreciated that the utility of the invention is not thus limited, but rather extends to any species which are covalently or associatively conjugatable in the manner of the invention, including, but not limited to: the following peptide species: calcitonin, ACTH, glucagon, somatostatin, somatotropin, somatomedin, parathyroid hormone, erythropoietin, hypothalmic releasing factors, prolactin, thyroid stimulating hormone, endorphins, antibodies, hemoglobin, soluble CD-4, clotting factors, tissue plasminogen activator, enkephalins, vasopressin, non-naturally occurring opioids, superoxide dismutase, interferon, asparaginase, arginase, arginine deaminease, adenosine deaminase ribonuclease, trypsin, chemotrypsin, and papain, alkaline phosphatase, and other suitable enzymes, hormones, proteins, polypeptides, enzyme-protein conjugates, antibody-hapten conjugates, viral epitopes, etc.; antivirals such as: Ara-A (Arabinofuranosyladenine), Acylguanosine, Nordeoxyguanosine, Azidothymidine, Dideoxyadenosine, and Dideoxycytidine; anti-cancer agents such as Dideoxyinosine Floxuridine, 6-Mercaptopurine, Doxorubicin, Daunorubicin, and I-darubicin; and antibiotic such as Erythormycin, Vancomycin, oleandomycin, and Ampicillin; antiarrhythmics such as Quinidine; and anticoagulants such as Heparins.

One objective of the present invention is to provide suitable polymers for conjugation with therapeutic agents so as to obtain the desirable characteristics enumerated above. Another objective is to utilize such modified therapeutic agents for sustained in vivo delivery of the therapeutic agent. Yet another objective is to use the technology to deliver therapeutic agents orally in their active form.

Yet another objective of the present invention is to provide amphiphilic prodrugs that are therapeutically effective by oral or parenteral administration.

A further objective is to employ associatively conjugated agents for use in immunoassay, diagnostic, and other non-therapeutic (e.g., in vitro ) applications. Still another objective of the present invention is to provide stabilizingly conjugated peptide and nucleoside compositions, including covalently bonded compositions variously suitable for in vivo as well as non-in vivo applications, and to alternatively provide non-covalent, associatively conjugated peptide and nucleoside compositions variously suitable for in vivo as well as non-in vivo applications.

Within the broad scope of the present invention, a single polymer molecule may be employed for conjugation with a plurality of therapeutic agent species, and it may also be advantageous in the broad practice of the invention to utilize a variety of polymers as conjugating agents for a given therapeutic agent; combinations of such approaches may also be employed. Further, stabilizingly conjugated therapeutic agent compositions may find utility in both in vivo as well as non-in vivo applications. Additionally, it will be recognized that the conjugating polymer(s) may utilize any other groups, moieties, or other conjugated species, as appropriate to the end use application. By way of example, it may be useful in some applications to covalently bond to the polymer a functional moiety imparting UV-degradation resistance, or antioxidation, or other properties or characteristics to the polymer. As a further example, it may be advantageous in some applications to functionalize the polymer to render same reactive or cross-linkable in character, to enhance various properties or characterisics of the overall conjugated material. Accordingly, the polymer may contain any functionality, repeating groups, linkages, or other constitutent structures which do not preclude the efficacy of the conjugated composition for its intended purpose. Other objectives and advantages of the present invention will be more fully apparent from the ensuing disclosure and appended claims.

Illustrative polymers that may usefully be employed achieve these desirable characteristics are described herein below in an exemplary reaction scheme. In covalently bonded peptide applications, the polymers may be functionalized and then coupled to free amino acid(s) of the peptide (s) to form lablie bonds which permit retention of activity with the lablie bonds intact. Removal of the bond by chemical hydrolysis and proteolysis then enhances the peptidal activity.

The polymers utilized in the invention may suitably incorporate in their molecules constituents such as edible fatty acids (lipophilic end), polyethylene glycols (water soluble end), acceptable sugar moieties (receptor interacting end), and spacers for therapeutic agent attachment. Among the polymers of choice, polysorbates are particularly preferred and are chosen to illustrate various embodiments of the invention in the ensuing discussion herein. The scope of this invention is of course not limited to polysorbates, and various other polymers incorporating above-described moieties may usefully be employed in the broad practice of this invention. Sometimes it may be desirable to eliminate one of such moieties and to retain others in the polymer structure, without loss of objectives. When it is desirable to do so, the preferred moieties to eliminate without losing the objectives and benefits of the invention are the sugar and/or the spacer moieties.

It is preferred to operate with polymers whose molecular weights fall between 500 and 10,000 daltons.

In the practice of the present invention, polyalkylene glycol residues of $C_2$–$C_4$ alkyl polyalkylene glycols, preferably polyethylene glycol (PEG), are advantageously incorporated in the polymer systems of interest.

The presence of these PEG residues will impart hydrophilic properties to the polymer and to the corresponding polymer-therapeutic agent conjugates. Certain glycolipids are known to stabilize therapeutic agents such as proteins and peptides. The mechanism of this stabilization probably involves association of the glycolipid fatty acid moieties with the hydrophobic domain of the peptide or protein; aggregation of the protein or peptide is thus prevented. It also is known that aggregated peptides are poorly absorbed in the small intestine compared to native peptides. The invention therefore contemplates polymer-peptide products in which the peptide, e.g., insulin, is conjugated with either the hydrophilic or hydrophobic residue of the polymer. The fatty acid portion of the polymer is provided to associate with the hydrophobic domain of the peptide and thus prevent aggregation in solution. The resulting polymer-peptide conjugates thus will be: stabilized (to chemical and enzymatic hydrolysis); water-soluble, due to the PEG residue; and, by virtue of the fatty acid-hydrophobic domain interactions, not prone to aggregation.

Polyalkylene glycol derivatization has a number of advantageous properties in the formulation of polymer-therapeutic agent conjugates in the practice of the present invention, as associated with the following properties of polyalkylene glycol derivatives: improvement of aqueous solubility, while at the same time eliciting no antigenic or immunogenic response; high degrees of biocompatibility; absence of in vivo biodegradation of the polyalkylene glycol derivatives; and ease of excretion by living organisms.

The polymers employed in the practice of the present invention thus comprise lipophilic and hydrophilic moieties, rendering the resulting polymer-drug conjugate highly effective (bioactive) in oral as well as parenteral and other modes of physiological administration. As used hereinafter, the terms "drug" and "therapeutic agent" are used interchangeably.

Set out below as illustrative examples of polymer-nucleoside conjugates of the present invention are the formulae of covalently bonded conjugates denoted for ease of subsequent reference as Conjugate 1, Conjugate 2, and Conjugate 3, wherein "drug" is insulin or other therapeutic agent, and specific values of m, n, w, x, and y will be described in the ensuing discussion.

Conjugate 1:

$R = C_4$–$C_{20}$; n = 1 to 125

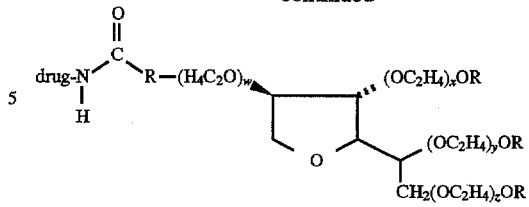

wherein:
w + x + y + z = 20; and

R = oleic acid: $CH_3(CH_2)_7CH=CH(CH_2)_7\overset{\underset{\parallel}{O}}{C}-$, or other fatty acid radicals from $C_4$–$C_{20}$.

Conjugate 2:

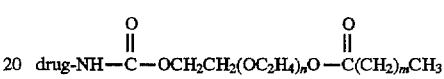

wherein: m and n each are idependently from 1 to 125.

Conjugate 3:

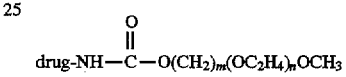

wherein: m and n each are independently from 1 to 125.

Conjugate 1 features commercially available polysorbate monooleate at the center of the polymeric system, a sugar derivative used in many pharmaceutical applications. Lipophilic and absorption enhancing properties are imparted by the fatty acid chain, while the polyethylene glycol (PEG) residues provide a hydrophilic (hydrogen bond accepting) environment. Drug is attached through a carbamate linkage adjacent to the PEG region of the polymer.

In Conjugate 2 the sugar residue is excluded, but drug is once again attached to the polymer through a carbamate bond adjacent to the hydrophilic PEG region of the polymer. The lipophilic fatty acid region of the polymer is thus some distance from the point of attachment to drug, e.g., insulin.

The arrangement described above for Conjugate 2 is reversed in the case of Conjugate 3. Once more the sugar residue is excluded, but in this structure the lipophilic fatty acid residue is closest to the point of attachment to drug and the hydrophilic PEG region is distant from the point of attachment, which again is through a carbamate bond.

Varied alignments of hydrophilic and lipophilic regions relative to the point of attachment of the polymer to the drug are possible in the broad practice of the invention, and such variation will result in polymers which provide lipophilic and hydrophilic domains to the drug. In Conjugates 1, 2, and 3 the point of attachment of the carbamate bond between the polymers is preferably the amine function.

In the general practice of the invention, various methods of coupling the polymers to the therapeutic agent, e.g., peptide, nucleoside, etc. are available and are discussed more fully hereinafter.

The polymers utilized in therapeutic agent conjugation in accordance with the invention are designed to incorporate good physical characteristics that enable them to achieve the desired objectives. Absorption enhancers, while enabling penetration of the drug through the cell membrane, do not improve the stability characteristics of the drug, and in vivo applications may therefore utilize the polymer-drug conjugates of the invention in formulations devoid of such penetration enhancers. One aspect of the present invention therefore relates to the incorporation of fatty moiety within the polymer, to mimic penetration enhancers.

In the covalently conjugated polymer-therapeutic agent conjugates of the present invention, the drug may be covalently attached to the water-soluble polymer by means of a lablie chemical bond. This covalent bond between the drug and the polymer may be cleaved by chemical or enzymatic reaction. The polymer-drug product retains an acceptable amount of activity; full activity of the component drug is realized when the polymer is completely cleaved from the drug. Concurrently, portions of polyethylene glycol are present in the conjugating polymer to endow the polymer-drug conjugate with high aqueous solubility and prolonged blood circulation capability. The modifications described above confer improved solubility, stability, and membrane affinity properties on the drug. As a result of these improved characteristics the invention contemplates parenteral and oral delivery of both the active polymer-drug species and, following hydrolytic cleavage, bioavailability of the drug per se, in in vivo applications.

The polymers used in the embodiment described below can be classified as polyethylene glycol modified lipids and polyethylene glycol modified fatty acids. Among preferred conjugating polymers may be mentioned polysorbates comprising monopalmitate, dipalmitate, tripalmitate, monolaurate, dilaurate, trialaurate, monooleate, dioleate, trioleate, monostearate, distearate, and tristearate. Other lower fatty acids can be utilized. The number average molecular weight of polymer resulting from each combination is preferred to be in the range of from about 750 to about 5,000 daltons. Alternative polymers of preference are polyethylene glycol ethers or esters of fatty acids, such fatty acids being lauric, palmitic, oleic, and stearic acids, other lower fatty acids can be utilized, and the polymers ranging from 250 to 5,000 daltons in number average molecular weight. It is preferred to have a derivatizable group in the polymer, where such group can be at the end terminating with polyethylene glycol or at the end terminating with fatty moiety. The derivatizable group may also be situated within the polymer and thus may serve as a spacer between the peptide and the polymer.

Several methods of modifying fatty acid sorbitan to achieve the desired polymer will be discussed in further detail with structural illustrations. Polysorbates are esters of sorbitols and their anhydrides, which are copolymerized with ethylene oxide. Shown below is the structure of a representative polymer.

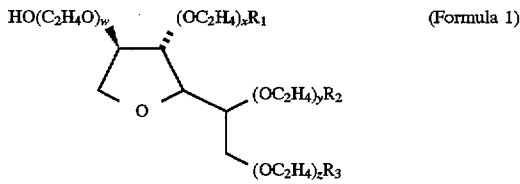

(Formula 1)

The sum of w, x, y, z is 20 and $R_1$, $R_2$ and $R_3$ are each independently selected from the group consisting of lauric, oleic, palmitic and stearic acid radicals, or $R_1$ and $R_2$ are each hydroxyl while $R_3$ is lauric, palmitic, oleic or stearic acid radical, or lower fatty acid. These polymers are commercially available and are used in pharmaceutical formulations. Where a higher molecular weight polymer is desired, it may be synthesized from glycolipids such as sorbitan monolaurate, sorbitan monooleate, sorbitan monopalmitate or sorbitan monostearate, and an appropriate polyethylene glycol. Structures of glycolipids which may be used as starting reagents are depicted below.

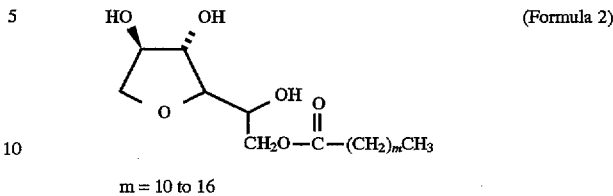

(Formula 2)

m = 10 to 16

In the synthesis of glycolipid polymers substituted in three positions with polyethylene glycol, a desired polyethylene glycol having two free hydroxyls at the termini is protected at one terminus with a trityl group in pyridine using one mole of trityl chloride. The remaining free hydroxyl group of the polyethylene glycol is converted to either tosylate or bromide. The desired glycolipid is dissolved in a suitable inert solvent and treated with sodium hydride. The tosylate or bromide of the protected polyethylene glycol is dissolved in inert solvent and added in excess to the solution of glycolipid. The product is treated with a solution of para-toluenesulfonic acid in anhydrous inert solvent at room temperature and purified by column chromatography. The structures of the transformation are depicted below.

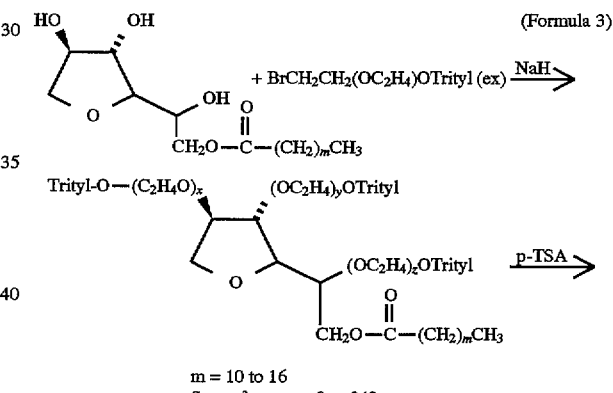

(Formula 3)

m = 10 to 16
Sum of x, y, z = 8 to 240

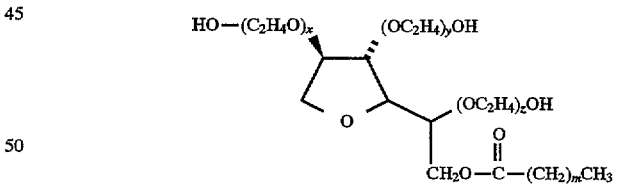

By adjusting the molar equivalent of reagents and using the appropriate molecular weight range of polyethylene glycol, mono or disubstituted glycolipids of the desired molecular weight range can be obtained by following the above procedures.

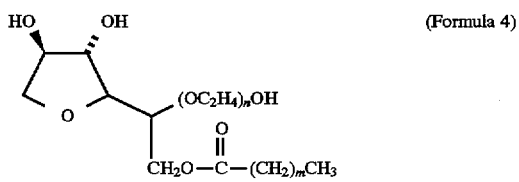

(Formula 4)

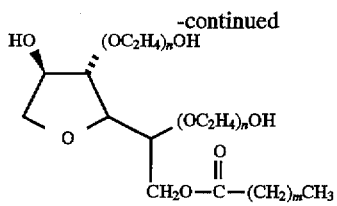

wherein each n and m may vary independently, and have any suitable value appropriate to the specific drug being stabilized, e.g., from 1 to 16.

The sugar portion of the glycolipid described above can be substituted with glycerol or aminoglycerol whose structural formulae are shown below.

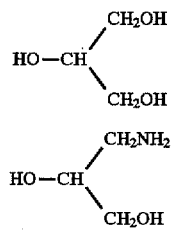

In this modification, the primary alcohol is first etherified or esterified with a fatty acid moiety such as lauric, oleic, palmitic or stearic; the amino group is derivatized with fatty acids to form amides or secondary amino groups, as shown below.

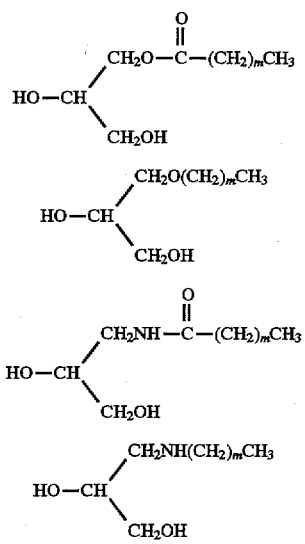

wherein m may have any suitable value, e.g., from 10 to 16.

The remaining primary alcohol group is protected with a trityl group while the secondary alcohol group is converted with polyethylene glycol to a desired polymer. Usually, the polyethylene glycol bears a leaving group at one terminal and a methoxy group at the other terminal. The polyethylene glycol is dissolved in inert solvent and added to a solution containing glycolipid and sodium hydride. The product is deprotected in para-toluenesulfonic acid at room temperature to give the desired polymer as depicted.

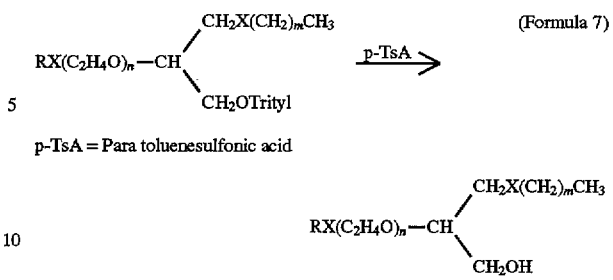

p-TsA = Para toluenesulfonic acid

Sometimes it is desirable to incorporate fatty acid derivatives in different parts of the polyethylene glycol chain to achieve certain physicochemical properties similar to polysorbates that have been substituted with two/three molecules of fatty acids, e.g., polysorbate trioleate.

Structures representing the polymers are shown in the reaction scheme below as the open chain of the polysorbate.

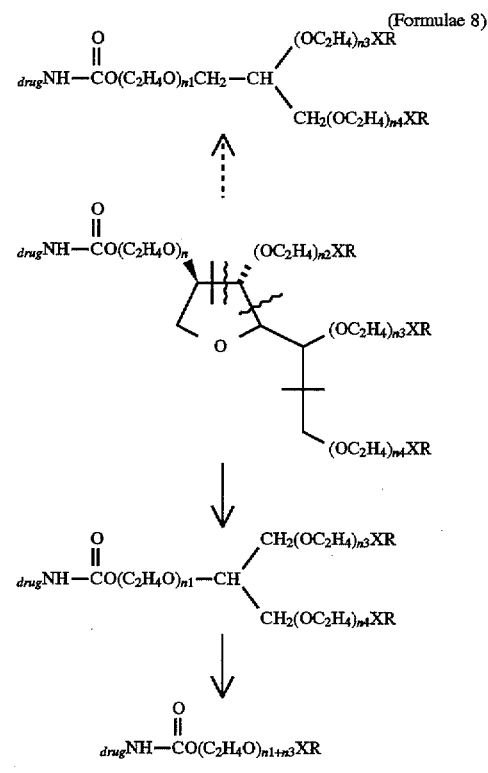

$R$ = Alkyl, $C_5$ to $C_{18}$;
$n$ = 5 to 120;

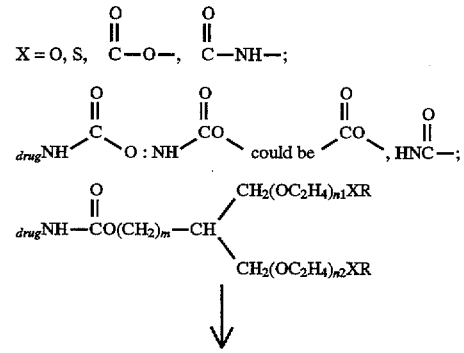

-continued

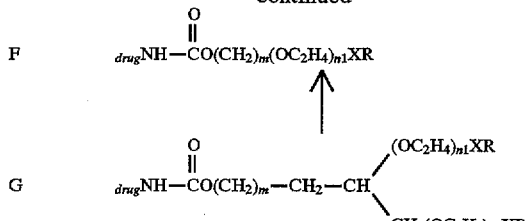

R = Alkyl, $C_5$ to $C_{18}$;
n = 5 to 120;
m = 2 to 15;

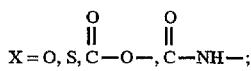

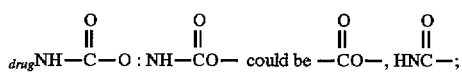

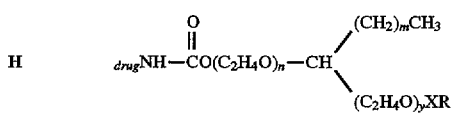

R = Alkyl, $C_5$ to $C_{18}$;
m = 5 to 18;
n = 2 to 15;
y = 5 to 120;
and wherein m, n, and y may be independently varied within the above ranges, relative to one another.

In the synthesis of polymer A, it is desirable to protect the hydroxyl moieties on the first and second carbon of glycerol, e.g. solketal. The remaining hydroxyl group is converted to the sodium salt in an inert solvent and reacted with halogenated or tosylated polyethylene glycol in which one end of the polyethylene glycol has been protected as an ester. The glycerol protection is removed and the resulting two free hydroxyl groups are converted to the corresponding sodium salts. These salts are reacted in inert solvent with polyethylene glycol which has been partially derivatized with fatty acids. Reaction takes place after the free hydroxyl is converted to the tosylate or bromide.

Polymer G is synthesized in the same manner except that the protected glycerol is first reacted with esters of fatty acids which have been halogenated at the terminal carbon of the acid.

In the synthesis of polymer C, it is preferable to start with 1,3-dihalo-2-propanol. The dihalo compound is dissolved in inert solvent and treated with the sodium salt of two moles of polyethylene glycol which has been previously derivatized with one mole of a fatty acid moiety. The product is purified by chromatography or dialysis. The resulting dry product is treated, in inert solvent, with sodium hydride. The sodium salt thus formed is reacted with a halo derivative of partially protected polyethylene glycol.

Sometimes it may be desired to omit the sugar portion of the polymer. The resulting polymer still contains a polyethylene glycol fragment. The membrane affinity properties of the fatty acid moiety may be retained by substituting a fatty acid proper with a lipophilic long chain alkane; biocompatibility is thus preserved. In one instance of this embodiment the polyethylene glycol with two terminal free hydroxyl groups is treated with sodium hydride in inert solvent. One equivalent weight of a primary bromide derivative of a fatty acid-like moiety is added to the polyethylene glycol solvent mixture. The desired product is extracted in inert solvent and purified by column chromatography if necessary.

Where it is desired to form an ester linkage between the fatty acid and the polyethylene glycol, the acid chloride of the acid is treated with excess of desired polyethylene glycol in suitable inert solvent. The polymer is extracted in inert solvent and further purified by chromatography if necessary.

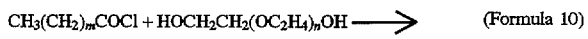

In some modifications of peptides, it is desired to conjugate the fatty acid moiety directly to the therapeutic agent. In this case the polymer is synthesized with the derivatizable function placed on the fatty acid moiety. A solution of mono-methoxypolyethylene glycol of appropriate molecular weight in inert solvent is treated with sodium hydride followed by the addition of solution containing the ethyl ester of afatty acid bearing a leaving group at the terminal carbon of the acid. The product is purified after solvent extraction and if necessary, by column chromatography.

The ester protection is removed by treating with dilute acid or base.

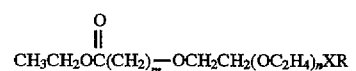

Where it is desired to form a carbamate bond with the the drug, the carboxyl or ester is converted to a hydroxyl group by a chemical reduction method known in the art.

The functional groups that are used in the drug conjugation are usually at a terminal end of the polymer, but in some cases, it is preferred that the functional group is positioned within the polymer. In this situation, the derivatizing groups serve as spacers. In one instance of this embodiment, a fatty acid moiety may be brominated at the carbon alpha to the carboxylic group and the acid moiety is esterified. The experimental procedure for such type of compound is similar to the one outlined above, resulting in the product shown below.

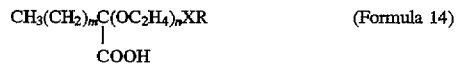

When an extended spacer is desired, a polyethylene glycol monoether may be converted to an amino group and treated with succinic anhydride that has been derivatized with a fatty acid moiety. A desired polyethylene glycol bearing primary amine is dissolved in sodium phosphate buffer at pH 8.8 and treated with a substituted succinic anhydride fatty acid moiety as shown in the scheme below.

The product is isolated by solvent extraction and purified by column chromatography if necessary.

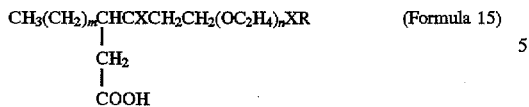
(Formula 15)

It is to be understood that the above reaction schemes are provided for the purposes of illustration only and are not to be limitingly construed in respect of the reactions and structures which may be beneficially utilized in the modification of the drug in the broad practice of the present invention, e.g., to achieve solubility, stabilization, and cell membrane affinity for parenteral and oral administration.

The reaction of the polymer with the drug to obtain covalently conjugated products is readily carried out. For the purpose of brevity in discussion herein, the polymer is referred to as (P). Where the polymer contains a hydroxyl group, it is first converted to an active carbonate derivative such as para-nitrophenyl carbonate. The activated derivative then is reacted with the amino residue of the drug in a short period of time under mild conditions producing carbamate derivatives.

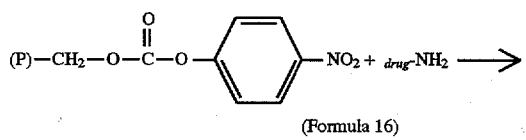
(Formula 16)

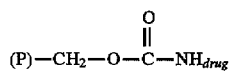

The above reaction and reagent only serve as illustration and are not exclusive; other activating reagents resulting in formation of urethane, or other, linkages can be employed. The hydroxyl group can be converted to an amino group using reagents known in the art. Subsequent coupling with drug through their carboxyl groups results in amide formation.

Where the polymer contains a carboxyl group, it can be converted to a mixed anhydride and reacted with the amino group of the drug to create a conjugate containing an amide bond. In another procedure, the carboxyl group can be treated with water-soluble carbodiimide and reacted with the drug to produce conjugates containing amide bonds.

The activity and stability of the drug conjugates can be varied in several ways, by using a polymer of different molecular size. Solubilities of the conjugates can be varied by changing the proportion and size of the polyethylene glycol fragment incorporated in the polymer composition. Hydrophilic and hydrophobic characteristics can be balanced by careful combination of fatty acid and polyethylene glycol moieties.

Set out below are some illustrative modification reactions for polymer-drug conjugates of the present invention.

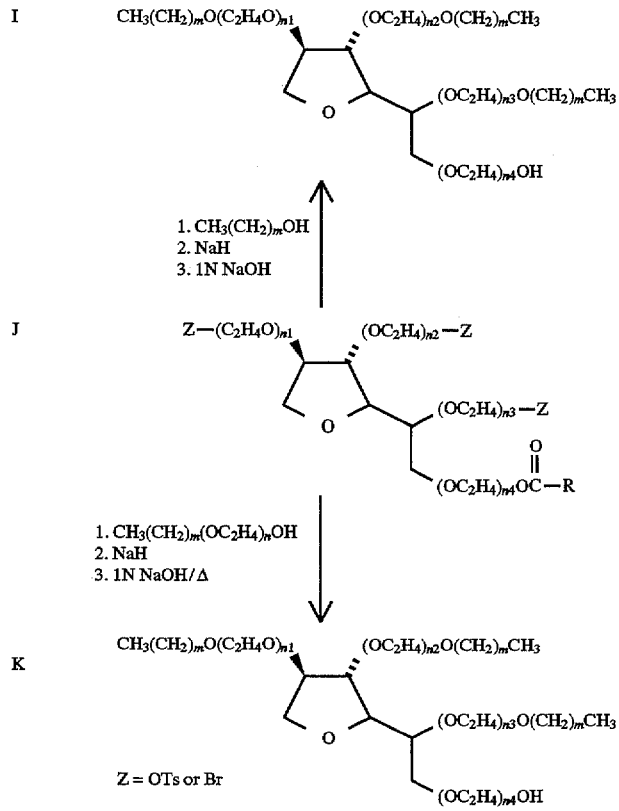

-continued

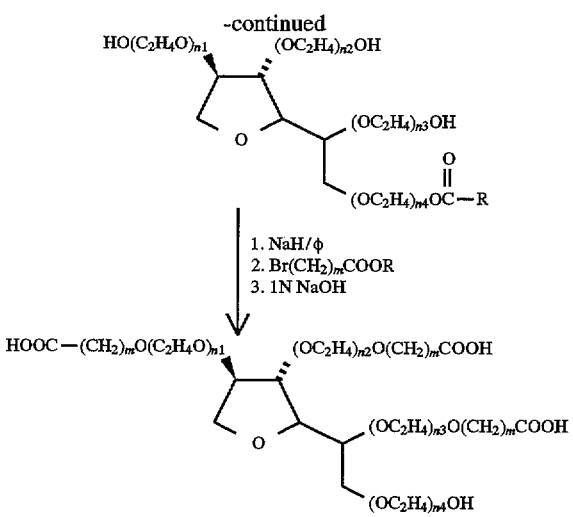

In the above reaction scheme involving species I, J and K, routes are demonstrated for modifying the hydrophilicity/lipophilicity balance of the conjugating polymer. Ester groups in the conjugating polymer are susceptible to non-hydrolysis by esterases; the conjugating polymer containing ester groups therefore may be modified to convert the ester groups to ether groups which are more hydrolysis-resistant in character. The reaction scheme involving L and M species illustrates the conversion of hydroxyl groups to carboxylate groups. In this respect, the carboxyl groups will provide carboxylate anion for conjugating amino residues of nucleosides or other drugs.

In general, various techniques may be advantageously employed to improve the stability characteristics of the polymer conjugates of the present invention, including: the functionalization of the polymer with groups of superior hydrolysis resistance, e.g., the previously illustrated conversion of ester groups to ether groups; modifying the lipophilic/hydrophilic balance of the conjugating polymer, as appropriate to the drug being stabilized by the polymer; and tailoring the molecular weight of the polymer to the appropriate level for the molecular weight of the drug being stabilized by the polymer.

The unique property of polyalkylene glycol-derived polymers of value for therapeutic applications of the present invention is general biocompatibility. The polymers have various water solubility properties and are not toxic. They are non-antigenic, non-immunogenic and do not interfere with biological activities of enzymes. They have long circulation in the blood and are easily excreted from living organisms.

The products of the present invention have been found useful in sustaining the biological activity of therapeutic nucleosides, peptides, and other therapeutic agents, and may for example be prepared for therapeutic administration by dissolving in water or acceptable liquid medium. Administration is by either the parenteral or oral route. Fine colloidal suspensions may be prepared for parenteral administration to produce a depot effect, or by the oral route.

In the dry, lyophilized state, the drug-polymer conjugates of the present invention have good storage stability; solution formulations of the conjugates of the present invention are likewise characterized by good storage stability.

The therapeutic polymer conjugates of the present invention may be utilized for the prophylaxis or treatment of any condition or disease state for which the drug constituent is efficacious.

In addition, the polymer-based conjugates of the present invention may be utilized in diagnosis of constituents, conditions, or disease states in biological systems or specimens, as well as for diagnosis purposes in non-physiological systems.

Further, the polymer conjugates of the invention may have application in prophylaxis or treatment of condition(s) or disease state(s) in plant systems. By way of example, the active component of the conjugate may have insecticidal, herbicidal, fungicidal, and/or pesticidal efficacy amenable to usage in various plant systems.

In therapeutic usage, the present invention contemplates a method of treating an animal subject having or latently susceptible to such condition(s) or disease state(s) and in need of such treatment, comprising administering to such animal an effective amount of a polymer conjugate of the present invention which is therapeutically effective for said condition or disease state.

Subjects to be treated by the polymer conjugates of the present invention include both human and non-human animal (e.g., bird, dog, cat, cow, horse) subjects, and preferably are mammalian subjects, and most preferably human subjects.

Depending on the specific condition or disease state to be combatted, animal subjects may be administered polymer conjugates of the invention at any suitable therapeutically effective and safe dosage, as may readily be determined within the skill of the art, and without undue experimentation.

The polymer-drug conjugates of the invention may be administered per se as well as in the form of pharmaceutically acceptable esters, salts, and other physiologically functional derivatives thereof.

The present invention also contemplates pharmaceutical formulations, both for veterinary and for human medical use, which comprise as the active agent one or more polymer conjugate(s) of the invention.

In such pharmaceutical and medicament formulations, the active agent preferably is utilized together with one or more pharmaceutically acceptable carrier(s) therefor and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired daily dose.

The formulations include those suitable for parenteral as well as non-parenteral administration, and specific administration modalities include oral, rectal, buccal, topical, nasal, ophthalmic, subcutaneous, intramuscular, intravenous, transdermal, intrathecal, intra-articular, intra-arterial, sub-arachnoid, bronchial, lymphatic, vaginal, and intra-uterine administration. Formulations suitable for oral and parenteral administration are preferred.

When the active agent is utilized in a formulation comprising a liquid solution, the formulation advantageously may be administered orally or parenterally. When the active agent is employed in a liquid suspension formulation or as a powder in a biocompatible carrier formulation, the formulation may be advantageously administered orally, rectally, or bronchially.

When the active agent is utilized directly in the form of a powdered solid, the active agent may advantageously be administered orally. Alternatively, it may be administered bronchially, via nebulization of the powder in a carrier gas, to form a gaseous dispersion of the powder which is inspired by the patient from a breathing circuit comprising a suitable nebulizer device.

The formulations comprising the active agent of the present invention may conveniently be presented in unit dosage forms and may be prepared by any of the methods well known in the art of pharmacy. Such methods generally include the step of bringing the active ingredient(s) into association with a carrier which constitutes one or more accessory ingredients. Typically, the formulations are prepared by uniformly and intimately bringing the active ingredient(s) into association with a liquid carrier, a finely divided solid carrier, or both, and then, if necessary, shaping the product into dosage forms of the desired formulation.

Formulations of the present invention suitable for oral administration may be presented as discrete units such as capsules, cachets, tablets, or lozenges, each containing a predetermined amount of the active ingredient as a powder or granules; or a suspension in an aqueous liquor or a non-aqueous liquid, such as a syrup, an elixir, an emulsion, or a draught.

A tablet may be made by compression or molding, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration conveniently comprise a sterile aqueous preparation of the active conjugate, which preferably is isotonic with the blood of the recipient (e.g., physiological saline solution). Such formulations may include suspending agents and thickening agents or other microparticulate systems which are designed to target the compound to blood components or one or more organs. The formulations may be presented in unit-dose or multi-dose form.

Nasal spray formulations comprise purified aqueous solutions of the active conjugate with preservative agents and isotonic agents. Such formulations are preferably adjusted to a pH and isotonic state compatible with the nasal mucus membranes.

Formulations for rectal administration may be presented as a suppository with a suitable carrier such as cocoa butter, hydrogenated fats, or hydrogenated fatty carboxylic acid.

Ophthalmic formulations are prepared by a similar method to the nasal spray, except that the pH and isotonic factors are preferably adjusted to match that of the eye.

Topical formulations comprise the active compound dissolved or suspended in one or more media, such as mineral oil, petroleum, polyhydroxy alcohols, or other bases used for topical pharmaceutical formulations.

In addition to the aforementioned ingredients, the formulations of this invention may further include one or more accessory ingredient(s) selected from diluents, buffers, flavoring agents, disintegrants, surface active agents, thickeners, lubricants, preservatives (including antioxidants), and the like.

Accordingly, the present invention contemplates the provision of suitable polymers for in vitro stabilization of drugs in solution, as a preferred illustrative application of non-therapeutic application. The polymers may be employed for example to increase the thermal stability and enzymic degradation resistance of the drug. Enhancement of the thermal stability characteristic of the drug via conjugation in the manner of the present invention provides a means of improving shelf life, room temperature stability, and robustness of research reagents and kits.

The following Examples are provided to illustrate the present invention, and should not be construed as limiting thereof.

EXAMPLE I

Conjugate 1

Polysorbate trioleate p-nitrophenyl carbonate

To a solution of p-nitrophenylchloroformate (0.8 g, 4 mmole) in 50 mL of anhydrous acetonitrile is added dry polysorbate trioleate (7 g, 4 mmole) followed by dimethylaminopyridine (0.5 g, 4 mmole). The reaction mixture is stirred at room temperature for 24 hours Solvent is removed under reduced pressure and the resultant precipitate is diluted with dry benzene and filtered through Celite. The residue is refrigerated overnight in dry benzene and the additional precipitate is removed by filtration. Solvent is removed under reduced pressure and residual benzene is removed by evacuation at low pressure to yield 6.4 g of polysorbate trioleate p-nitrophenyl carbonate.

Coupling of insulin with activated polymer

To a solution of activated polysorbate trioleate (1 g) in aqueous mixture of dimethylsulfoxide (DMSO) or dimethylformamide (DMF) is added a solution of bovine insulin (50 mg) in 0.1M pH 8.8 phosphate buffer. pH is maintained by addition of 1N NaOH as necessary. The reaction mixture is stirred at room temperature for 2.5 h. After this time the mixture is subjected to gel filtration chromatography using Sephadex G-75. Purification by elution with 0.1M pH 7.0 phosphate buffer and collection of fractions with an automated fraction collector yields Conjugate 1. The polymer content is determined by trinitrobenzenesulfonic acid (TNBS) assay and mass spectrometry, and the protein concentration by Biuret Method. A molar ratio of polymer to insulin is determined to be 1:1. Conjugate I is also obtained by using pure organic sovent (e.g., DMSO, DMF).

EXAMPLE II

Conjugate 2

The terminal hydroxyl group of polyethylene glycol monostearate is activated by reaction with p-nitrophenyl chloroformate as described above. To a solution of the activated polymer (1 g) in distilled water is added bovine insulin (80 mg) dissolved in 0.1M phosphate buffer, at pH 8.8. The pH is maintained by careful adjustment with 1N NaOH. After stirring for 3 hours, the reaction mixture is quenched with excess glycine and subjected to gel filtration chromatography using Sephadex G-75. Insulin/polymer conjugate is collected and lyophilized. Protein content is determined by Biuret assay, giving a quantitative yield.

EXAMPLE III

Conjugate 3

Tetrahydro-2-(12-bromododecanoxy)-2H pyran

To a solution of 12-bromo-1-dodecanol (1 mole) in dichloromethane containing pyridinium p-toluenesulfonate (P-TSA) is added dihydropyran (2 moles). The reaction mixture is stirred for 24 hours and then washed twice with water and dried over anhydrous $MgSO_4$. The dichloromethane is removed under reduced pressure. If necessary the resulting product is purified by chromatography on silica gel.

Coupling of polyethylene glycol to the terahydropyran derivative

The tetrahydropyran derivative described above, dissolved in dry benzene, is added to a solution of polyethylene glycol (1 mole) in dry benzene containing NaH (1 mole). The reaction mixture is stirred at room temperature for 24 hours. After that time the mixture is eluted through a silica gel column with benzene. Additional purification by column chromatography, if necessary, is performed. The protective tetrahydropyran group is removed by treatment with p-TSA at room temperature. The final product is purified, if necessary, by column chromatography. The hydroxyl group of the polymer is activated by reaction with p-nitrophenylchloroformate as described hereinabove. Conjugation with insulin is carried out as described for Conjugate 1.

EXAMPLE IV

Comparative studies using bovine insulin were conducted on polymer-insulin conjugates and on native insulin to determine their relative stability and activity in animal models. In the animal studies, the efficacy of the polymer-insulin in lowering the blood level was compared to that of native insulin. Female and male albino mice averaging 25 g in weight were fasted overnight and used in groups of five for each treatment conducted in several phases over a period of two days.

Each test animal received a single dose of either native insulin (Group 1,100 µg/kg, subcutaneously); native insulin (Group 2, 1.5 mg/kg, orally by gavage); Conjugate 1) Group 3, 100 µg/kg, orally); or Conjugate 1 (Group 4, 100 µg/kg, subcutaneously) at time 0. An additional group (Group 5) received no insulin of any kind but was challenged with glucose 30 minutes before scheduled sampling times. Animals were fasted overnight before treatment and for the duration of the study. All test materials were prepared in phosphate buffered saline, pH 7.4. Thirty minutes before scheduled sampling times of 0.5, 1,2, 4, 8 and 24 hours following treatment with insulin, animals were challenged with a bolus dose of glucose (5 g/kg, as a 50% solution, given orally), so that each animal received only one dose of insulin or Conjugate 1 and one glucose challenge. At the scheduled sample time blood was collected from the tail vein and immediately analyzed for glucose content using a One Touch Digital Glucose Meter (Life Scan). The results of the test are shown in FIG. 1, for Groups 1–5.

Blood glucose levels for Group 1 animals (native insulin, subcutaneous) were approximately 30% of control (Group 5, untreated) animals at the 30 minute time point. This hypoglycemic effect lasted only 3.5 hours in Group 1 animals. Native insulin administered orally (Group 2) lowered blood glucose levels to a maximum of 60% of control, this maximum response occurring 30 minutes after treatment with the insulin. In contrast the glucose levels in animals in Group 3 (Conjugate 1, 100 µg/kg, p.o.) were lowered with an apparent delayed onset of hypoglycemic activity. The hypoglycemic activity in Group 3 animals was greater than that in Group 2 animals even though the dose of insulin administered to Group 3 was only one fifteenth of that given to Group 2. At all time points after 3 hours glucose levels were lower for Group 3 animals than for any other treatment group, the largest difference being at the four to eight hour sampling points. Glucose levels in Group 4 animals (Conjugate 1,100 µg/kg, s.c.) followed the same course as those for Group 1 animals for the first four hours of the study. After four hours Group2 glucose levels remained above control (untreated, Group 5) levels whereas Group 4 glucose levels dropped, at eight hours, to 62% of Group 5 levels, and remained below Group 5 levels.

EXAMPLE V

An insulin efficacy study was conducted on male and female albino mice using as test materials insulin in unconjugated form, and Conjugate 1. One objective of this study was to determine whether insulin in the form of Conjugate 1 is capable of acting on blood glucose levels in the same way as insulin when administered subcutaneously. A second objective was to determine whether the insulin complex of Conjugate 1, unlike free insulin, is capable of acting to decrease the blood glucose level when administered orally. The results are shown in FIG. 2, wherein "Insulin Complex" denotes Conjugate 1.

Baseline blood samples were obtained for serum glucose analysis from 10 fasted untreated albino mice (5 males and 5 females); baseline values in FIG. 2 are denoted by the symbol "0". Three additional groups (five males and five females each) were fasted overnight and loaded with glucose alone orally by gavage (5 g/kg body weight). Ten animals were sacrificed at each of three time periods to obtain blood samples for glucose analysis: 30, 60 and 120 minutes after dosing. A commerial insulin and Conjugate 1 were each administered both orally (p.o) and parenterally (s.c.) to groups of fasted mice (five males and five females, for sacrifice and blood analysis at each of the three time periods), to provide different treatment regimens. The treatment, administration routes, symbols shown for results in FIG. 2 included: (i) glucose (5 g/kg p.o.), symbol: "●"; (ii) insulin (100 µg/kg, s.c.) and glucose (5 g/kg p.o.), symbol: "▽"; (iii) insulin (1.5 mg/kg, p.o.) and glucose (5 g/kg p.o.), symbol: "▼"; (iv) Conjugate 1 (100 µg/kg, s.c.) and glucose (5 g/kg p.o.), symbol –□"; (v) Conjugate 1 (250 µg/kg, s.c.) and glucose (5 g/kg p.o.), symbol: "■"; (vi) Conjugate 1 (1.5 mg/kg, s.c.) and glucose (5 g/kg p.o.), symbol: "Δ". In these tests of Conjugate 1, the concentration of the protein in the administered solution was 0.1 mg protein/ml solution; for comparison purposes, a modified covalently bonded insulin-polymer conjugate, having a protein concentration in the administered solution of 0.78 mg protein/ml solution, was included, (vii) modified Conjugate 1 (1001 µg/kg, s.c.) and glucose (5 g/kg p.o.), symbol: "▲".

The insulin was administered 15 minutes prior to glucose loading.

Glucose was administered orally by gavage to all but the baseline group of animals at a dose of 5 g/kg (10 mg/kg of a 50% w/v solution in normal saline). When insulin was administered orally by gavage, it was given at a dose of 1.5 mg/kg (18.85 ml/kg of a 0.008% w/v solution in normal saline). When insulin was administered subcutaneously, it was given at a dose of 1001 µg/kg (2.5 ml/kg of a 0.004% w/v solution in normal saline). When the Conjugate 1 polymer-insulin complex was administered orally by gavage, it was given at a dose of 1.56 mg/kg (2.0 ml/kg of the undiluted test material). When the Conjugate 1 polymer-insulin complex was administered subcutaneously, it was given at a dose of 100 µg/kg (1.28 ml/kg of a 1:10 dilution of the 0.78 mg/ml solution received) or 250 µg/kg (3.20 ml/kg of a 1:10 dilution of the solution received). The modified Conjugate 1 contained 0.1 ml insulin/ml and was dosed at a rate of 1.0 ml/kg to obtain a 100 µg/kg dose.

Glucose was measured using the Gemini Centrifugal Analyzer and purchased glucose reagent kits. The assay was a coupled enzymatic assay based on the reaction of glucose and ATP catalyzed by hexokinase, coupled with the glucose-6-phosphate dehydrogenase reaction, yielding NADH. Duplicate samples were analyzed and the mean value reported. Dilution (1:2 or 1:4) of some serum samples was necessary in order to determine the very high glucose concentration present in certain samples.

After glucose loading, mean serum glucose rose to a high level at 30 minutes, declined at 60 minutes, and was below baseline at 120 minutes. If commercial insulin was administered subcutaneously (100 µg/kg body weight, it was highly effective in preventing the increase in blood glucose. However, if insulin was given orally (at a high dose of 1.5 mg/kg) there was no effect on the rise of blood glucose. This was expected, since insulin, a protein, is readily hydrolyzed in the digestive tract and is not absorbed intact into the bloodstream.

When Conjugate 1 was given subcutaneously at either 100 or 250 µg/kg dosage, it was highly effective in restricting the rise in blood glucose after glucose loading. Mean serum glucose values were significantly lower after the 100 µg/kg dose of Conjugate 1 at both 30 and 60 minutes than they were after 100 µg/kg of free insulin. Mean serum glucose at 250 µg/kg of Conjugate 1 was lower, though not significantly, at 30 minutes, significantly lower at 60 minutes and at 120 minutes was returned to the baseline. With both free insulin at 100 µg/kg and Conjugate 1 at 100 µg/kg, the glucose level remained below baseline at 120 minutes.

The modified Conjugate 1 administered at 100 µg/kg produced a significant reduction in blood glucose at 30 minutes.

EXAMPLE VI

Preparation of Para-Nitrophenyl Carbonate of Polysorbate Monopalmitate

Polysorbate monopalmitate is first dried by the azeotropic method using dry benzene.

To a solution of the dry polymer (2 g, 2 mmole) in 10 ml of dry pyridine is added para-nitrophenylchloroformate (0.6 g, 3 mmol). The mixture is stirred at room temperature for 24 hours. The reaction mixture is chilled in ice and diluted with dry benzene and filtered through filter aid. This procedure is repeated and finally the solvent is removed at the rotary evaporator. Traces of solvent are removed in vacuo. The yield of the product is 1.8 g.

EXAMPLE VII

Preparation of Polysorbate Monopalmitate Conjugate with Insulin

In accordance with the previously described conjugation reaction procedure of Example I but using polysorbate monopalmitate in the amount of 1 g and insulin in the amount of 80 mg, with HPLC separation of the reaction product, an insulin-polysorbate monopalmitate covalently bonded conjugate is obtained.

EXAMPLE VIII

Preparation of Enzyme-polymer Conjugates

Coupling of alkaline phosphatase (AP) to polymer was carried out using the same procedure as described for Conjugate 1 in Example I. In addition, to determine whether a high or low ratio of polymer to protein would be more advantageous, conjugates were prepared using 140 moles of polymer/mole of enzyme and 14 moles of polymer/mole of enzyme. The number of polymer groups per molecule of conjugated AP are 30 and 5, respectively, for the high and low ratios of polymer.

The following procedure was employed to obtain about 5 groups/molecule of alkaline phosphatase: 4.1 mg (salt free) was dissolved in 0.05M. sodium bicarbonate. To this solution was added activated polymer (0.75 mg) in water/dimethyl-sulfoxide and the solution was stirred for 3 to 12 hours at room temperature. The resulting reaction mixture was dialyzed against a salt solution (0.3N NaCl) in dialysis tubing (MW cutoff 12,000–14,000) over 12 hours with 4 to 6 changes of dialysis solution. The same procedure was used for the high ratio. Total protein concentration of dialyzed material was determined by Biuret method.

Activity Measurement and Stability Study

The phophatase assay was performed according to the method of A. Voller et al, Bulletin WHO, 53, 55 (1976). An aliquot (50 microliter) was added to microwells and mixed with 200 microliter of substrate solution (10 g/L, 4-nitrophenylphosphate in 20% ethanolamine buffer, pH 9.3) and incubated at room temperature for 45 minutes. The reaction was stopped by 50 microliter of 3M NaOH. The absorbance was measured at 405 nm in a micro plate reader.

Phosphatase activity was compared with that of native enzyme under various conditions.

Dilute solutions containing similar concentrations of alkaline phosphatase and alkaline phosphatase-polymer conjugates were stored at various temperatures. The enzymatic activity was tested periodically. The two polymers tested at 5° C., 15° C., 35° C. and 55° C. were compared to the control alkaline phosphatase stored at 5° C.

As can be seen from Table A, the initial enzymatic activity of both polymers was about three-fold higher than the control. Both polymer-enzyme conjugates had enhanced thermal stability over the native enzyme. This is especially evident for the conjugate characterized by the higher ratio of polymer to enzyme.

TABLE A

| TEMP, °C. | DAY | | | | | |
|---|---|---|---|---|---|---|
| | 0 | 2 | 3 | 4 | 5 | 6 |
| AP/HIGH | | | | | | |
| 5 | 399 | 360 | 321 | 371 | 343 | 337 |
| 15 | | 158 | 115 | 126 | 24 | 184 |
| 35 | | 132 | 112 | 135 | 138 | 123 |
| 55 | | 36 | 25 | 10 | 14 | |
| AP/LOW | | | | | | |
| 5 | 324 | 252 | 210 | 220 | 162 | 159 |
| 15 | | 83 | 47 | 40 | 38 | 51 |
| 35 | | 61 | 36 | 35 | 33 | 32 |
| 55 | | 17 | 6 | 2 | 2 | |
| AP/CONTROL | | | | | | |
| 5 | 100 | 100 | 100 | 100 | 100 | 100 |
| 15 | | 89 | 74 | 43 | 36 | 28 |
| 35 | | 53 | 48 | 21 | 20 | 20 |
| 55 | | 10 | 2 | 1 | 2 | |

EXAMPLE IX

Conjugate 1A

To a solution of insulin (50 mg) in 0.05M sodium bicarbonate buffer of pH 9.2 is added a solution of activated polymer (1 g) in water/dimethylsulfoxide and stirred for 3 hours, at room temperature. The pH of the mixture is maintained by careful adjustment with 1N NaOH. The reaction mixture then is dialyzed against 0.1M pH 7.0 phosphate buffer. Purified product is lyophilized. Protein content (48 mg) is determined by Biuret assay. The number of polymer chains linked to insulin is determined by TNBS assay, giving a ratio of two moles of polymer to one mole of insulin.

EXAMPLE X

Synthesis Of $OT_{10C}$-AraCMP

Synthesis of tributylAraCMP:

A mixture of 200 mg of AraCMP (0.62 mmole), 1 ml of pyridine, 161 µl of tri-n-butylamine (0.67 mmole) and 1.1 ml of anhydrous butyric-anhydride (6.2 mmole) was stirred for 21 hours at room temperature. Methanol (1 ml) was added to the reaction mixture to destroy unreacted butyric anhydride and stirred for 1 hour. The reaction mixture was then stirred with water (0.5 ml) for 24 hours at room temperature to cleave the butyric phosphate bond. After rolo-evaporating the solvent, the product, tributylAraCMP was extracted into 10 ml of chloroform and the organic layer was washed with 3×15 ml of water. The chloroform layer was dried over $MgSO_4$ and evaporated to dryness. This product was used in the next step without further purification.

Conjugation of $OT_{10}C$ (polyoxyethylene [10]cetylether) to tributylAraCMP.

TPSCl (1.3 mmole) was dissolved in 6 ml of anhydrous chloroform and added to tributylAraCMP and stirred for 40 minutes at room temperature. The resulting TPS activated tributylAraCMP was added to 876 mg of $OT_{10}$ (1.2 mmole) in 2.1 ml of pyridine and stirred at room temperature for 4½ hours. TLC of the reaction mixture in THF: methanol (10:0.75 v/v) showed complete disappearance of tributylated AraCMP. The solvent was evaporated and the product was suspended in 6 ml water and extracted into 2×6 ml of chloroform.

The butyl groups of the $OT_{10}$ conjugated AraCMP were deprotected by stirring the chloroform layer with 4.5 ml of 2.0M ammonia solution in ethanol overnight at room temperature.

Purification of $OT_{10}$Conjugated AraCMP

Solvent was rotoevaporated from the reaction mixture above and TPS sulfonic acid was precipitated with 15 ml water. The pH of the aqueous layer was reduced to 1–2 and the product was extracted into 6×35 ml of chloroform. HPLC of the chloroform layer on an analytical C8 column in isopropanol-water-0.1% TFA showed a hydrophobic nucleoside product. $^{31}$PNMR of the product shows attachment of a polymeric residue to the phosphate moiety and $^1$H NMR shows the polymeric as well as the nucleoside resonances. The product was purified on C-8 column with isopropanol-water 0.1% TFA gradient.

While the invention has been described herein, with certain features, and embodiments it will be recognized that the invention may be widely varied, and that numerous other modifications, variations, and other embodiments are possible, and such modifications, variations, and other embodiments are to be regarded as being within the spirit and scope of the invention.

What is claimed is:

1. A composition comprising a therapeutic agent stabilizingly and covalently conjugatively coupled with one or more molecules of a non-naturally-occurring polymer, said polymer comprising a lipophilic moiety and a hydrophilic polymer moiety, thereby imparting balanced lipophilic and hydrophilic characteristics to the composition such that the composition is soluble in pharmaceutically acceptable solvents and able to interact with biological membranes.

2. A composition according to claim 1, wherein the therapeutic agent comprises a peptide.

3. A composition according to claim 1, wherein the therapeutic agent comprises a nucleoside.

4. A composition comprising a therapeutic agent stabilizingly and conjugatively coupled with one or more molecules of a non-naturally-occurring polymer comprising a lipophilic moiety and a hydrophilic polymer moiety wherein the therapeutic agent is soluble in aqueous solvents and active in prophylaxis or treatment of conditions or disease states in a mammalian subject.

5. A peptide composition according to claim 4, wherein the non-naturally-occurring polymer comprises (i) a linear polyalkylene glycol moiety and (ii) a lipophilic moiety.

6. A composition according to claim 1, wherein the therapeutic agent is a diagnostic peptide used for reactively determining the presence or absence of a condition or component in vitro or in vivo.

7. A composition according to claim 1, wherein the therapeutic agent is active in a plant or component thereof.

8. A composition according to claim 1, wherein the non-naturally-occurring polymer comprises (i) a linear polyalkylene glycol moiety and (ii) a lipophilic moiety.

9. A composition according to claim 1, wherein the therapeutic agent comprises an antineoplastic agent.

10. A composition according to claim 1, wherein:

the non-naturally-occurring polymer comprises (i) a linear polyalkylene glycol moiety and (ii) a lipophilic moiety;

the therapeutic agent comprises a physiologically active agent selected from the group consisting of peptides, proteins, nucleosides, nucleotides, antiviral agents, antineoplastic agents, antibiotics, antiarrhythmics, and anticoagulants; and the physiologically active agent, the linear polyalkylene glycol moiety and the lipophilic moiety are conformationally arranged in relation to one another such that the physiologically active agent in the composition has an enhanced in vivo resistance to enzymatic degradation, relative to the physiologically active agent alone.

11. A physiologically active therapeutic agent composition comprising a physiologically active therapeutic agent covalently coupled with one or more molecules of a polymer comprising (i) a linear polyalkylene glycol moiety and (ii) a lipophilic moiety, wherein the physiologically active therapeutic agent, the linear polyalkylene glycol moiety and the lipophilic moiety are conformationally arranged in relation to one another such that the physiologically active therapeutic agent in the physiologically active therapeutic agent composition has an enhanced in vivo resistance to enzymatic degradation, relative to the physiologically active therapeutic agent alone.

12. A physiologically active therapeutic agent composition of three-dimensional conformation comprising a physiologically active therapeutic agent covalently coupled with a polysorbate complex comprising (i) a linear polyalkylene glycol moiety and (ii) a lipophilic moiety, wherein the physiologically active therapeutic agent, the linear polyalkylene glycol moiety and the lipophilic moiety are conformationally arranged in relation to one another such that (a) the lipophilic moiety is exteriorly available in the three-dimensional conformation, and (b) the physiologically active therapeutic agent in the physiologically active therapeutic agent composition has an enhanced in vivo resistance to enzymatic degradation, relative to the physiologically active therapeutic agent alone.

13. A multiligand conjugated therapeutic agent complex comprising a triglyceride backbone moiety, having:

a bioactive therapeutic agent covalently coupled with the triglyceride backbone moiety through a polyalkylene glycol spacer group bonded at a carbon atom of the triglyceride backbone moiety; and at least one fatty acid moiety covalently attached either directly to a carbon atom of the triglyceride backbone moiety or covalently joined through a polyalkylene glycol spacer moiety.

14. A multiligand conjugated peptide complex according to claim 13, wherein the α' and β carbon atoms of the triglyceride bioactive moiety have fatty acid moieties attached by covalently bonding either directly thereto, or indirectly covalently bonded thereto through polyalkylene glycol spacer moieties.

15. A multiligand conjugated peptide complex according to claim 13, wherein the fatty acid moiety is covalently attached either directly or through a polyalkylene glycol spacer moiety to the α and α' carbons of the triglyceride backbone moiety, with the bioactive therapeutic agent being covalently coupled with the β-carbon of the triglyceride backbone moiety, either being directly covalently bonded thereto or indirectly bonded thereto through a polyalkylene spacer moiety.

16. A polysorbate complex comprising a polysorbate moiety including a triglyceride backbone having a fatty acid group covalently coupled to one of the α,α' and β carbon atoms thereof, and having a polyethylene glycol group covalently coupled to one of the α,α' and β carbon atoms thereof, wherein the polysorbate moiety has a physiological active nucleoside covalently bonded thereto.

17. A polysorbate complex according to claim 16, wherein the nucleoside is an antiviral nucleoside.

18. A polysorbate complex according to claim 16, wherein the physiologically active moiety is covalently bonded to the polyethylene glycol group.

19. A stable, aqueously soluble, conjugated therapeutic agent complex comprising a therapeutic agent stabilizingly and conjugatively coupled to a polyethylene glycol modified glycolipid moiety.

20. A complex according to claim 19, wherein the therapeutic agent is covalently coupled to the polyethylene glycol modified glycolipid moiety by a lablie covalent bond at a free amino acid group of the therapeutic agent, wherein the lablie covalent bond is scissionable in vivo by biochemical hydrolysis and/or proteolysis.

21. A complex according to claim 19, wherein the polyethylene glycol modified glycolipid moiety comprises a polysorbate polymer.

22. A complex according to claim 21, wherein the polysorbate polymer comprises fatty acid ester groups selected from the group consisting of monopalmitate, dipalmitate, monolaurate, dilaurate, trilaurate, monoleate, dioleate, trioleate, monostearate, distearate, and tristearate.

23. A complex according to claim 19, wherein the polyethylene glycol modified glycolipid moiety comprises a polymer selected from the group consisting of polyethylene glycol ethers of fatty acids, and polyethylene glycol esters of fatty acids, wherein the fatty acids comprise a fatty acid selected from the group consisting of lauric, palmitic, oleic, and stearic acids.

24. A complex according to claim 19, wherein the therapeutic agent comprises an agent selected from the group consisting of Ara-A (Arabinofuranosyladenine), Acylguanosine, Nordeoxyguanosine, Azidothymidine, Dideoxyadenosine, Dideoxycytidine, Dideoxyinosine Floxuridine, 6-Mercaptopurine, Doxorubicin, Daunorubicin, I-darubicin, Erythormycin, Vancomycin, oleandomycin, Ampicillin, Quinidine and Heparin.

25. A complex according to claim 19, comprising a polysorbate moiety including a triglyceride backbone having a fatty acid group covalently coupled to one of the α,α' and β carbon atoms thereof, and having a polyethylene glycol group covalently coupled to one of the α,α 'and β carbon atoms thereof.

26. A complex according to claim 25, wherein the therapeutic agent is covalently coupled with the triglyceride backbone at the β carbon atom thereof.

27. A complex according to claim 19, wherein the therapeutic agent is a nucleoside.

28. A complex according to claim 25, wherein the triglyceride backbone comprises a biocompatible divalent spacer group between the β carbon atom and one of the α,α' carbon atoms of the triglyceride backbone.

29. A polysorbate complex comprising a polysorbate moiety including a triglyceride backbone having covalently coupled to carbon atoms independently selected from α,α' and β carbon atoms thereof, functionalizing groups including:

(i) a fatty acid group; and (ii) a polyethylene glycol group having a physiologically active nucleoside moiety covalently bonded thereto.

30. A polysorbate complex according to claim 29, wherein the physiologically active nucleoside moiety is covalently bonded to a terminal functionality of the polyethylene glycol group.

31. A therapeutic agent composition according to claim 1, wherein the polymer has a molecular weight of from about 500 to about 10,000 daltons.

32. A therapeutic agent composition according to claim 1, wherein the therapeutic agent is selected from the group consisting of Ara-A (Arabinofuranosyladenine), Acylguanosine, Nordeoxyguanosine, Azidothymidine, Dideoxyadenosine, Dideoxycytidine, Dideoxyinosine Floxuridine, 6-Mercaptopurine, Doxorubicin, Daunorubicin, I-darubicin, Erythormycin, Vancomycin, oleandomycin, Ampicillin, Quinidine and Heparin.

33. A composition according to claim 1, wherein the therapeutic agent comprises Azidothymidine.

34. A polymer-therapeutic agent conjugate comprising a conjugating polymer selected from the group consisting of polymers of the formulae:

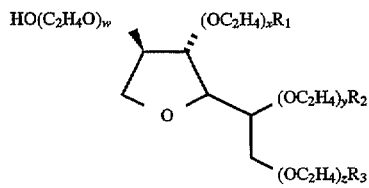

wherein the sum of w, x, y, z is from 4 to 100 and $R_1$, $R_2$ and $R_3$ are each independently selected from the group consisting of lauric, oleic, palmitic and stearic acid radicals and $C_5$–$C_{18}$ alkyl, or $R_1$ and $R_2$ are each hydroxyl while $R_3$ is lauric, palmitic, oleic or stearic acid radical;

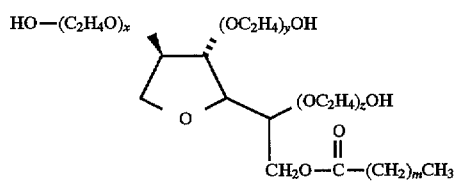

wherein:
m=10 to 16, and the
sum of x, y, z=8 to 240

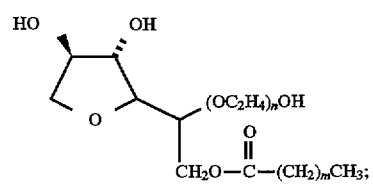

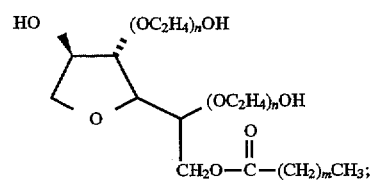

wherein m has a value from 10 to 16, n+m is 8–240, or when more than one n is present, the sum of all n's+m is 8–240, and wherein the sugar portion of the glycolipid is optionally substituted with glycerol or aminoglycerol;

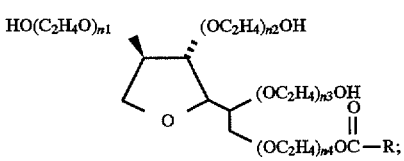

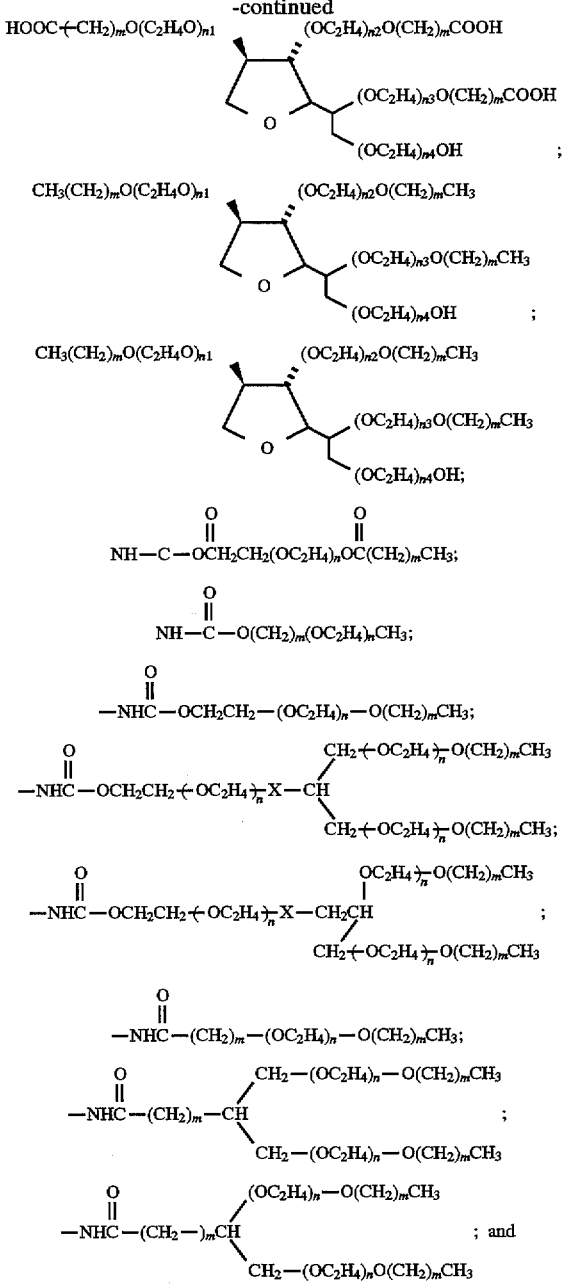

wherein x=O and wherein: m and n are specified above; and wherein said polymer is conjugatively coupled to a therapeutic agent.

35. A method of prophylactically or interventionally treating a potential or developed condition or disease state in a human or non-human mammalian subject with a therapeutic agent effective therefor, comprising administering to the subject an effective amount of a conjugated therapeutic agent composition comprising a stable, aqueously soluble, conjugated therapeutic agent complex comprising said therapeutic agent coupled to a physiologically compatible polyethylene glycol modified glycolipid moiety.

36. A method of prolonging the activity of a therapeutically active agent in an in vivo or in vitro system, comprising conjugatively coupling said therapeutic agent with one or more molecules of a non-naturally-occurring polymer comprising a lipophilic moiety and a hydrophilic polymer moiety to yield a conjugatively coupled polymer-therapeutic agent composition, and introducing the conjugatively coupled polymer-therapeutic agent composition to the in vivo or in vitro system.

37. A composition according to claim 1, wherein said therapeutic agent comprises an agent selected from the group consisting of:

calcitonin, ACTH, glucagon, somatostatin, somatotropin, somatomedin, parathyroid hormone, erythropoietin, hypothalmic releasing factors, prolactin, thyroid stimulating hormone, endorphins, antibodies, hemoglobin, soluble CD-4, clotting factors, tissue plasminogen activator, enkephalins, vasopressin, non-naturally occurring opioids, superoxide dismutase, interferon, asparaginase, arginase, arginine deaminease, adenosine deaminase ribonuclease, trypsin, chemotrypsin, and papain, alkaline phosphatase, enzyme-protein conjugates, antibody-hapten conjugates and viral epitopes.

38. A physiologically active therapeutic agent composition according to claim 11, wherein said active therapeutic agent comprises an agent selected from the group consisting of:

calcitonin, ACTH, glucagon, somatostatin, somatotropin, somatomedin, parathyroid hormone, erythropoietin, hypothalmic releasing factors, prolactin, thyroid stimulating hormone, endorphins, antibodies, hemoglobin, soluble CD-4, clotting factors, tissue plasminogen activator, enkephalins, vasopressin, non-naturally occurring opioids, superoxide dismutase, interferon, asparaginase, arginase, arginine deaminease, adenosine deaminase ribonuclease, trypsin, chemotrypsin, and papain, alkaline phosphatase, enzyme-protein conjugates, antibody-hapten conjugates and viral epitopes.

39. A physiologically active therapeutic agent composition according to claim 12, wherein said active therapeutic agent comprises an agent selected from the group consisting of:

calcitonin, ACTH, glucagon, somatostatin, somatotropin, somatomedin, parathyroid hormone, erythropoietin, hypothalmic releasing factors, prolactin, thyroid stimulating hormone, endorphins, antibodies, hemoglobin, soluble CD-4, clotting factors, tissue plasminogen activator, enkephalins, vasopressin, non-naturally occurring opioids, superoxide dismutase, interferon, asparaginase, arginase, arginine deaminease, adenosine deaminase ribonuclease, trypsin, chemotrypsin, and papain, alkaline phosphatase, enzyme-protein conjugates, antibody-hapten conjugates and viral epitopes.

40. A multiligand conjugated therapeutic agent complex according to claim 13, wherein said bioactive therapeutic agent comprises an agent selected from the group consisting of:

calcitonin, ACTH, glucagon, somatostatin, somatotropin, somatomedin, parathyroid hormone, erythropoietin, hypothalmic releasing factors, prolactin, thyroid stimulating hormone, endorphins, antibodies, hemoglobin, soluble CD-4, clotting factors, tissue plasminogen activator, enkephalins, vasopressin, non-naturally occurring opioids, superoxide dismutase, interferon, asparaginase, arginase, arginine deaminease, adenosine deaminase ribonuclease, trypsin, chemotrypsin, and papain, alkaline phosphatase, enzyme-protein conjugates, antibody-hapten conjugates and viral epitopes.

41. A complex according to claim 19, wherein said therapeutic agent comprises an agent selected from the group consisting of:

calcitonin, ACTH, glucagon, somatostatin, somatotropin, somatomedin, parathyroid hormone, erythropoietin, hypothalmic releasing factors, prolactin, thyroid stimulating hormone, endorphins, antibodies, hemoglobin, soluble CD-4, clotting factors, tissue plasminogen activator, enkephalins, vasopressin, non-naturally occurring opioids, superoxide dismutase, interferon, asparaginase, arginase, arginine deaminease, adenosine deaminase ribonuclease, trypsin, chemotrypsin, and papain, alkaline phosphatase, enzyme-protein conjugates, antibody-hapten conjugates and viral epitopes.

42. A polymer-therapeutic agent conjugate according to claim 34, wherein said therapeutic agent comprises an agent selected from the group consisting of:

calcitonin, ACTH, glucagon, somatostatin, somatotropin, somatomedin, parathyroid hormone, erythropoietin, hypothalmic releasing factors, prolactin, thyroid stimulating hormone, endorphins, antibodies, hemoglobin, soluble CD-4, clotting factors, tissue plasminogen activator, enkephalins, vasopressin, non-naturally occurring opioids, superoxide dismutase, interferon, asparaginase, arginase, arginine deaminease, adenosine deaminase ribonuclease, trypsin, chemotrypsin, and papain, alkaline phosphatase, enzyme-protein conjugates, antibody-hapten conjugates and viral epitopes.

43. A method according to claim 35, wherein said therapeutic agent comprises an agent selected from the group consisting of:

calcitonin, ACTH, glucagon, somatostatin, somatotropin, somatomedin, parathyroid hormone, erythropoietin, hypothalmic releasing factors, prolactin, thyroid stimulating hormone, endorphins, antibodies, hemoglobin, soluble CD-4, clotting factors, tissue plasminogen activator, enkephalins, vasopressin, non-naturally occurring opioids, superoxide dismutase, interferon, asparaginase, arginase, arginine deaminease, adenosine deaminase ribonuclease, trypsin, chemotrypsin, and papain, alkaline phosphatase, enzyme-protein conjugates, antibody-hapten conjugates and viral epitopes.

44. A method according to claim 36, wherein said therapeutically active agent comprises an agent selected from the group consisting of:

calcitonin, ACTH, glucagon, somatostatin, somatotropin, somatomedin, parathyroid hormone, erythropoietin, hypothalmic releasing factors, prolactin, thyroid stimulating hormone, endorphins, antibodies, hemoglobin, soluble CD-4, clotting factors, tissue plasminogen activator, enkephalins, vasopressin, non-naturally occurring opioids, superoxide dismutase, interferon, asparaginase, arginase, arginine deaminease, adenosine deaminase ribonuclease, trypsin, chemotrypsin, and papain, alkaline phosphatase, enzyme-protein conjugates, antibody-hapten conjugates and viral epitopes.

* * * * *

UNITED STATES PATENT AND TRADEMARK OFFICE
CERTIFICATE OF CORRECTION

PATENT NO. : 5,681,811
DATED : October 28, 1997
INVENTOR(S) : Nnochiri N. Ekwuribe It is certified that error appears in the above-indentified patent and that said Letters Patent is hereby corrected as shown below:

```
Column 2,  line 21    change "micelies" to -- micelles --
Column 7,  line 42    change "γ-carbon" to -- β-carbon --
Column 8,  line 16    change "lablie" to -- labile --
Column 8,  line 18    change "lablie" to -- labile --
Column 9,  line 11    change "greate" to -- greater --
Column 9,  line 11    after "greater" insert -- than about 10,000,
                      wherein the --
Column 12, line 51    change "lablie" to -- labile --
Column 12, line 52    change "lablie" to -- labile --
Column 31, line 46    change "rolo" to -- roto --
Column 34, line 5     change "lablie" to -- labile --
Column 34, line 7     change "lablie" to -- labile --
```

Signed and Sealed this

Twenty-third Day of June, 1998

*Attest:*

BRUCE LEHMAN

*Attesting Officer*      *Commissioner of Patents and Trademarks*